(12) United States Patent
Naboulsi

(10) Patent No.: US 11,079,847 B2
(45) Date of Patent: *Aug. 3, 2021

(54) HANDS ON WHEEL CONTROL WITH DIGITAL ICONS

(71) Applicant: Mouhamad A. Naboulsi, Detroit, MI (US)

(72) Inventor: Mouhamad A. Naboulsi, Detroit, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/108,904

(22) Filed: Jan. 11, 2019

(65) Prior Publication Data
US 2019/0324542 A1    Oct. 24, 2019

Related U.S. Application Data

(63) Continuation of application No. 15/352,220, filed on Nov. 15, 2016, now Pat. No. 10,331,212, which is a
(Continued)

(51) Int. Cl.
*H04M 1/60* (2006.01)
*H04B 1/38* (2015.01)
(Continued)

(52) U.S. Cl.
CPC ............... *G06F 3/016* (2013.01); *A61B 5/18* (2013.01); *B60R 11/02* (2013.01);
(Continued)

(58) Field of Classification Search
CPC ...... H04B 1/3833; H04B 1/38; H04B 1/3822; H04M 1/6075; H04M 1/6083;
(Continued)

(56) References Cited

U.S. PATENT DOCUMENTS 6,526,460 B1 * 2/2003 Dauner .................. G01C 21/26
701/48
9,575,971 B2 * 2/2017 Hampiholi .......... G06F 16/4387
(Continued)

*Primary Examiner* — Quochien B Vuong
(74) *Attorney, Agent, or Firm* — The Weintraub Group, P.L.C.

(57) ABSTRACT

The present invention provides a safety control system for a vehicle with controls located on the vehicle steering wheel. The controls maybe arranged in a cluster on one or both sides of the upper half of the steering wheel. The controls can be located in areas of the steering wheel including the spokes, the rim or a special flange extended from the rim or the spoke of the steering wheel and are easily recognizable and accessible by the driver while the driver is looking ahead from a normal driving position with the driver's eyes focused on the road and maintaining the driver's hands on the steering wheel. The controls can be further enhanced by varied coloring, shape, size, and texture to make them easily identifiable. The controls can be used to access and control vehicle systems or portable telematics devices in multi modal process in conjunction with thumb gesture interpretation or speech recognition. A further enhancement to the system is the introduction of a universal portable devices docking station to eliminate falling devices and the consequences of accident.

19 Claims, 28 Drawing Sheets

Related U.S. Application Data continuation of application No. 14/296,834, filed on Jun. 5, 2014, now Pat. No. 9,526,447.

(51) Int. Cl.
*H04M 1/00* (2006.01)
*G06F 3/01* (2006.01)
*B60R 11/02* (2006.01)
*G08B 21/06* (2006.01)
*A61B 5/18* (2006.01)
*G06F 3/0488* (2013.01)
*B60R 11/00* (2006.01)

(52) U.S. Cl.
CPC ...... *B60R 11/0264* (2013.01); *G06F 3/04883* (2013.01); *G08B 21/06* (2013.01); *B60R 2011/001* (2013.01); *G06F 2203/04101* (2013.01); *H04M 1/6075* (2013.01)

(58) Field of Classification Search
CPC .......... H04M 1/72527; H04M 1/72463; H04L 12/40; H04L 2209/80; H04L 2209/84; B60L 3/0084; B60L 2250/16; B60L 2250/22; A61B 5/18; B60R 11/02; B60R 11/0264; B60R 21/06; G06F 3/016; G06F 3/04883
USPC ............ 455/345, 411, 556.1, 557, 565, 567, 455/569.1, 569.2, 575.9; 340/411, 438, 340/527, 575, 576, 901; 701/36
See application file for complete search history.

(56) References Cited

U.S. PATENT DOCUMENTS

| | | | |
|---|---|---|---|
| 10,064,081 B2* | 8/2018 | Lee | H04M 1/72527 |
| 2002/0142727 A1* | 10/2002 | Hsu | B60R 25/102 455/345 |
| 2014/0094228 A1* | 4/2014 | Hamelink | H04M 1/6091 455/569.2 |
| 2014/0371987 A1* | 12/2014 | Van Wiemeersch | B62D 1/04 701/41 |
| 2018/0224844 A1* | 8/2018 | Zhang | H04L 67/125 |

* cited by examiner

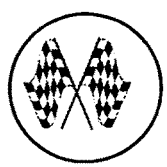  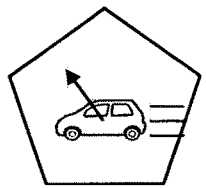 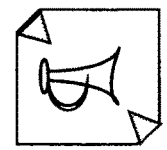 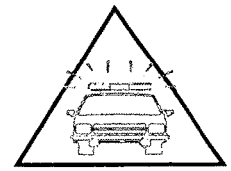
Fig. 17A   Fig. 17B   Fig. 17C   Fig. 17D   Fig. 17E
Fig. 17

51  52

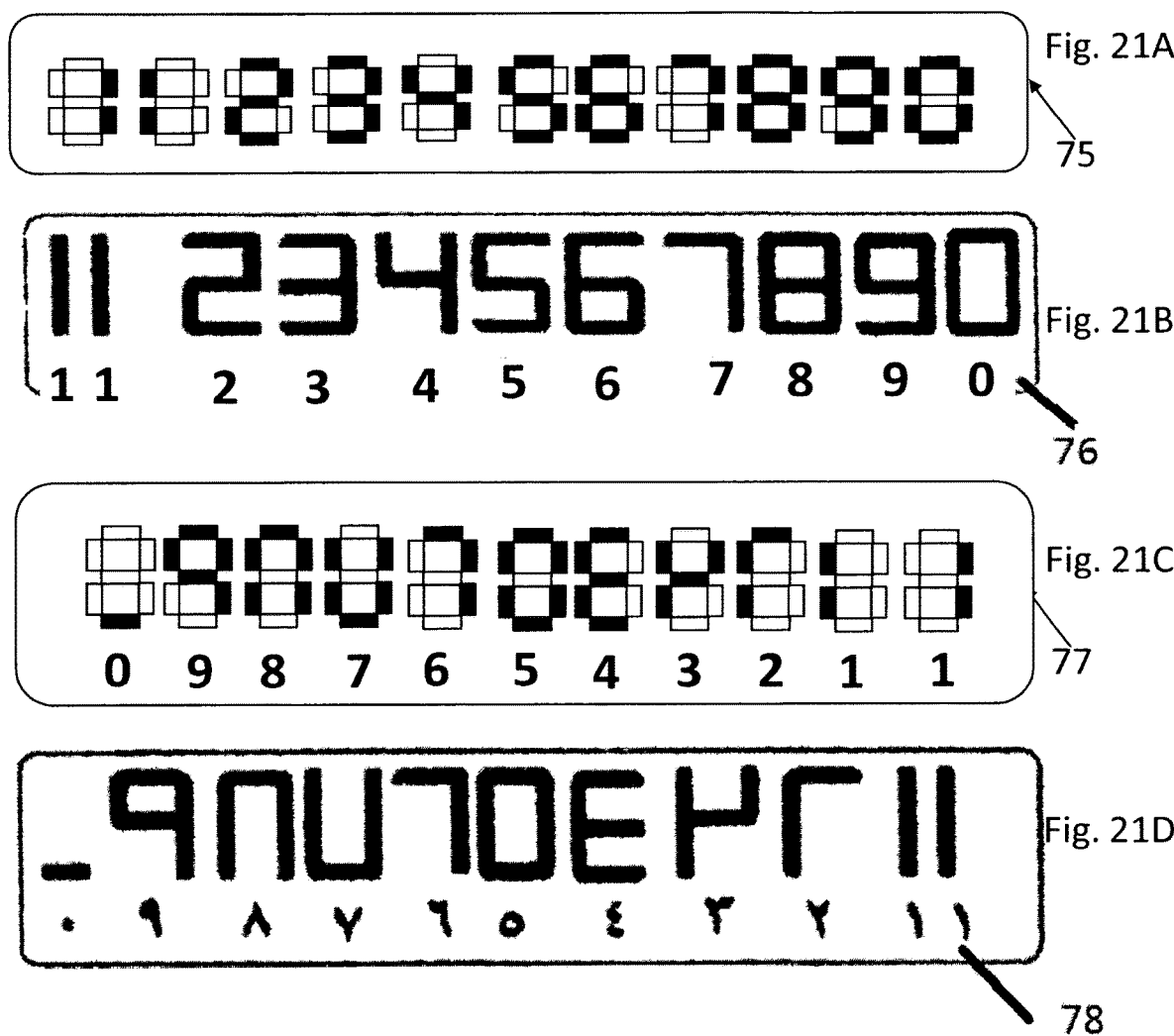
Fig. 21A — 75
Fig. 21B — 76
Fig. 21C — 77
Fig. 21D — 78

HANDS ON WHEEL CONTROL WITH DIGITAL ICONS

REFERENCE TO CO-PENDING APPLICATIONS

The present application claims the benefit of the filing date of U.S. nonprovisional application Ser. No. 15/352,220 which claims the benefit of U.S. provisional patent application Ser. No. 61/446,179 filed on Feb. 24, 2011, the contents of which are hereby incorporated by reference in its entirety; and the present application is a continuation-in-part of and claims the benefit of the filing date of U.S. copending nonprovisional application Ser. No. 10/338,708 filed on May 4, 2004, the contents of which are hereby incorporated by reference in its entirety, which is a continuation of and claims the benefit of the filing date of U.S. nonprovisional application Ser. No. 10/287,299 filed on Nov. 4, 2002 and issued as U.S. Pat. No. 8,731,925 on May 4, 2004, the contents of which are hereby incorporated by reference in its entirety, which is a continuation-in-part of and claims the benefit of the filing date of U.S. nonprovisional application Ser. No. 10/279,447 filed on Oct. 24, 2002, the contents of which are hereby Incorporated by reference in its entirety, which claims the benefit of the filing date of U.S. provisional patent application 60/390,877 filed on Jun. 21, 2002 and U.S. provisional application 60/336,293 filed on Oct. 24, 2001; the contents of all of which are hereby incorporated by reference in their entireties.

BACKGROUND OF THE INVENTION

The technological complexity and number of available features and options of driver operated vehicles has increased greatly with the passage of time. These features, often relating to in-car electronics, consumer electronics, mobile devices, telematics devices and related software applications may create distractions impeding the safe operation of the vehicle by the driver. This problem is exasperated with the fact that vehicles and consumer electronics are not intended for mix use by the driver while driving. These distractions are summarized by three categories, Eyes Off The Road, e.g. looking at a display, Hands Off The Wheel, e.g. texting or dialing, reaching for a moving object in the vehicle, e.g. Finding and grabbing an unsecured mobile phone when it rings. Accordingly, it is imperative and one of the goals of this invention to minimize those distractions by providing a safety control system for a vehicle with controls located on the vehicle steering member (i.e. steering wheel) that are accessible by the driver while maintaining the drives hands on the wheel and eyes on the road. These controls may communicate commands and/or data to and from a controller that communicates commands and/or data to and from a vehicle bus or portable telematic devices through other communication protocols.

Other functions that complement this invention are the addition of Guided Thumb Gesture Interpretation sensor as opposed to the previously disclosed free hand Thumb Gesture Interpretation that can be used to enter physical commands or alphanumeric text right from the controls noted above.

Other functions that complement this invention is in conjunction with this invention is the addition of a cradle that can hold the portable devices securely to eliminate visual and falling objects distractions.

Dangerous driving conditions can occur, for example, when drivers reach out to control vehicle accessories, dial a portable telephone, or change destination on a navigation device. The dangers can arise when the driver takes his eyes off the road to operate these mentioned devices and/or features causing the driver to lose track of any new developments and/or changes in the traffic or the road conditions surrounding the vehicle. These dangers are exasperated because the driver may remove one or both hands from the steering wheel to operate these device and/or features thereby maintaining only one or no hands on the steering wheel (steering member). Having one hand on the steering wheel may cause the arm holding the wheel to move unknowingly to the driver (i.e. the crosses extensor reflex).

A driver who is distracted while driving increases the possibility of an accident. A distraction can be anything that diverts the driver's attention from the primary tasks of navigating the vehicle and responding to critical events. Distractions include anything that takes a driver's eyes off the road (visual distraction), a driver's mind off the road (cognitive distraction), or a driver's hands off the wheel (manual distraction).

Current and previous National Highway Traffic Safety Administration (NHTSA) research, studies, and reports (as further discussed in U.S. Pat. No. 6,731,925 issued on May 4, 2004 incorporated in its entirety by reference), including the following: Distraction Effects of InVehicle Tasks Requiring Number and Text Entry Using Auto Alliance's Principle 2.1B Verification Procedure, February 2012, DOT HS 811 571; Developing a Test to Measure Distraction Potential of In-Vehicle Information System Tasks in Production Vehicles, November 2011, DOT HS 811 463; Distraction Effects of Manual Number and Text Entry While Driving, August 2011, DOT HS 811 510; An Analysis of Driver Inattention Using a Case-Crossover Approach On 100-Car Data: Final Report, May 2010, DOT HS 811 334; NHTSA Distracted Driving Research Plan, April 2010, DOT-HS-811-299; Measuring Distraction Potential of Operating In-Vehicle Devices, December 2009, DOT-HS-811-231; Driver Distraction Review of Current State of Knowledge, April 2008, DOT-HS-810-787; Driver Strategies for Engaging in Distracting Tasks Using In-Vehicle Technologies, March 2008, DOT HS 810 919; Characteristics of Voice-Based Interfaces for InVehicle Systems and Their Effects on Driving Performance; March 2007, DOT-HS-810-867; The Impact of Driver Inattention on Near-Crash/Crash Risk: An Analysis Using the 100-Car Naturalistic Driving Study Data, April 2006, DOT HS 810 594; The 100-Car Naturalistic Driving Study, Phase II—Results of the 100-Car Field Experiment, April 2006, DOT HS 810 593; An Overview of The 100-Car Naturalistic Driving Study and Findings, June 2005. NHTSA Paper No. 05-0400; Assessment of Truck Driver Distraction Problem and Research Needs, May 2005, DOT HS 809 883; On-Road Study of Willingness to Engage in Distracting Tasks, March 2005, DOT HS 809 863; Wireless Phone and AutoPC Related Technology: Driver Distraction and Use Effects on the Road, November 2004, DOT HS 809 752; The Effects of Voice Technology on Test Track Driving Performance; Implications for Driver Distraction, December 2003, DOT HS 809 525; Volume 1: Findings—National Survey of Distracted and Drowsy Driving Attitudes and Behavior—2002, March 2003; In Vehicle Inventory of Technologies: Human Factors Design Characteristics, February 2002, DOT HS 809 457; Driver Workload Metrics Project: Final Report, November 2006, DOT HS 810 635; Driver Workload Metrics Project: Final Report—Appendices, November 2006, DOT HS 810 635; Traffic Safety Facts—Research Note: An Examination of Driver Distraction as Recorded in NHTSA Databases, September 2009 DOT HS 811 216; Traffic Safety Facts—Research Note:

Driver Electronic Device Use, September 2009, DOT HS 811 184; Examination of the Distraction Effects of Wireless Phone Interfaces Using the National Advanced Driving Simulator—Final Report on a Freeway Study, June 2005, DOT HS 809 787; Hand-Held or Hands-free? The Effects of Wireless Phone Interface Type On Phone Task Performance and Driver Preference, June 2005; A Bibliography of Research Related to the Use of Wireless Communications Devices From Vehicles, February 2005; Wireless Phone and AutoPC Related Technology: Driver Distraction and Use Effects on the Road, November 2004. DOT HS 809 752; Examination of the Distraction Effects of Wireless Phone Interfaces Using the National Advanced Driving Simulator—Preliminary Report on a Freeway Scenario Study, April 2004. DOT HS 809 737; NHTSA Report: Driver Distraction with Wireless Telecommunications and Route Guidance Systems, July 2000, DOT HS 809 069; NHTSA Wireless Communications Report: An Investigation of the Safety Implications of Wireless Communications in Vehicles, November 1997; (all the above are incorporated in their entireties by reference), investigate and address how distractions impact driver performance, and develop and evaluate vehicle-based counter measures to minimize the effects thereof by wire throttle control).

The above referenced "Naturalistic Driving" publication indicates that driver conversation is not the source of a driving distraction, rather, the looking away to perform a tasks is the cause of accidents. Therefore to avoid the driver having to look away to perform a task, advocates of speech recognition technology attempted to solve this problem by having the driver speak a command to a computer and having the computer then perform the task. Unfortunately, due to the shortfalls of speech recognition, this has been mainly unsuccessfully implemented partially because of and has shown real world failures to meet manufacture reliability standards. (See *Many Cars Tone Deaf To Women's Voices*, May 31, 2011. Sharon Silke Carty, published at aol.com).

To reduce driver distraction, governmental authorities have enacted legislation requiring that telephones used in vehicles by drivers while driving must be of the "Hands Free" type; telematics equipment also include a warning and discouraging the driver about the risk of using these devices while driving. However, such legislation is difficult to enforce and education is not usually effective in assuring driver compliance over a short time spans as evidenced by the Safety Belt campaign and the intoxicated driving campaign.

Moreover, even where the vehicle is equipped with a "Hands Free" telephone, drivers nevertheless still frequently use one hand for holding or dialing the telephone because speech recognition's poor reliability or because the Hands Free system they are using is not equipped to provide dialing or answering features. When one hand is occupied by holding a telephone, the danger of causing an accident in an emergency situation is increased because of the additional reaction time required to properly grip the steering wheel with both hands. Similar danger exists when the driver attempts to control audio and video equipment (e.g. Radio. Music CD, DVD. Books on tape etc.), or when the driver attempts to change environmental controls like adjusting the heat or air conditioning and/or other vehicle settings. These controls traditionally require diversion of vision off the driving direction and travel and lead to increasing the likelihood of accidents.

The present invention focuses on maintaining the driver's hands on the wheel and eyes on the road while providing the driver a control system for safely operating desired portable devices, vehicle functions and/or features using Short Cut controls and/or Thumb Gesture Interpretation as a system to detect the Gesture and a s to conform vehicle and portable telematics device controls to accept common gesture as a command so as to reduce cognitive workload of the driver while operating any vehicle function, accessories or portable telematics devoices. As per University of South Carolina research, Dr. Amit Almor-Department of Psychology, speech has a cognitive workload on the person as they began to speak, so the gesture of Yes, No are much less taxing if a person is involved in a task with multiple steps while doing something critical such as driving.

One goal of the invention is to take advantage an enhance the capabilities of various sensorial driver abilities, provide the tools necessary to the driver to accomplish risky tasks in a new safer manner and reduce the possibility of falling phones and MP3 player which is a known causes for distraction, accidents and death. The sensorial abilities are enhanced by allowing the driver to obtain more information in a single glance or through peripheral vision by using, for example, color, shape, to enhance the peripheral visual recognition, dermal/tactile sensation, to select a function or a feature and confirming driver intent with tactile, haptic or atltJ.ic verbal and visual feedback to minimize driver distraction while maintaining the driver's hand on the wheel and eyes on the road. Another goal of the invention is allow the driver to input commands using natural Thumb Gesture response, e.g. Thumbs Up. Thumb Down, Next, etc. and to enhance the gesture system by introducing a Guided Gesture that allows the driver to enter alphanumeric character in a language of choice and. Lastly, a known cause of accidents is the falling cellular phone and portable devices while driving. This is alleviated by introducing a universal cradle that is shaped like a pocket and can accept and grip any shape device without the need for a manual adjustment.

BRIEF SUMMARY OF THE INVENTION

The present invention meets some or all of the above-mentioned needs by providing a driver operated vehicle control system that is operable by the driver of the vehicle while maintain the driver's hands on the steering wheel and the driver's eyes on the road thereby limiting distractions that may arise from the driving having to remove one or both hands from the steering wheel and/or the drivers eyes from the road. One aspect of the vehicle control system provides one or more control clusters disposed or located on one or more upper portions of a vehicle steering member, thereby placing the controls within the peripheral vision of the driver while the driver's eyes are focused on the road where the peripheral vision of a driver with healthy vision is almost 180-degree forward-facing horizontal field of view, and the vertical range of the field of view is typically around 100 degrees. These control clusters may have one or more distinct shortcut actuators for selecting or activating one or more menu selections for one or more devices or vehicle functions. The menu selections may include one or more submenus, options, or commands that are verbally or visually communicated to the driver by the control system. One or more response actuators using Thumb Gesture can be present for affirming, skipping or rejecting a control system communicated submenus, options, or commands. The shortcut actuators and can be accessible by a thumb of the driver of the vehicle while both hands of the driver remain in contact with the steering member eliminated the need for the driver to remove any hand off the steering wheel. The control cluster is monitored by a program, preferences, adjustment or settings thus the controller and the control cluster for a system that the driver maintain his hands on the wheel. The shortcut actuator and response actuators using Thumb Gesture using Thumb Gesture may communicate commands and/or data with a controller. The controller communicates commands and/or data, through a physical and/or wireless protocol with a vehicle communication bus of the vehicle, other controllers and/or devices. The control system can send information and receive information, commands, inquires, and/or data from the shortcut and response actuators, vehicle bus, controllers, and/or devices. The control system operated by the driver can control devices such as one or more vehicle function, equipment for use by disabled drivers, vehicle components, or features, one or more portable telematics devices, or any combination thereof, without the driver having to remove the driver's hands from the steering wheel or eyes from the round. For example, these devices can include, but are not limited to, phones, music players, video players, navigation systems; radios, vehicle windows, vehicle door locks, vehicle windshield wipers, vehicle cruise control, vehicle horn, vehicle climate and/or environmental controls, vehicle sun/moon roof, vehicle communication devices, vehicle lighting, environmental controls, infotainment, safety equipment such as lighting, signaling and vehicle windshield wipers or actual driving functions such as acceleration and accelerator pedal and breaking and breaking pedal and steering and steering member. Such acceleration or breaking or steering or gear shifting can be accomplished by a Drive By Wire technology where any of the actuated part of the vehicle include an actuator, electric or pneumatic, that is responsive to an electrical signal), and other similar devices, accessories and/or features that can be found in and/or used in vehicles. As a reference, Driveby-wire, DbW, by-wire, or x-by-wire technology in the automotive industry replaces the traditional mechanical control systems with electronic control systems using electromechanical actuators and human-machine interfaces such as pedal and steering feel emulators. Hence, the traditional components such as the steering column, intermediate shafts, pumps, hoses, belts, coolers and vacuum servos and master cylinders are eliminated from the vehicle. Examples include electronic throttle control and brake-by-wire. This is currently used in electric forklifts and stockpickers and some tractors [1]. Its implementation in road vehicles is limited by concerns over reliability although it has been demonstrated in several concept vehicles such as ThyssenKrupp Presta Steering's Mercedes-Benz Unimog. General Motors' Hy-wire and Sequel and the Mazda Ryuga. A rear wheel SbW system by Delphi called Quadrasteer is used on some pickup trucks but has had limited commercial success. This is not to be confused with Electric Power Steering.

The response actuators using Thumb Gesture can be activated physically or verbally by the driver; therefore, speech recognition can play a role in communication between the driver, the control system, and/or the vehicle.

To help facilitate, simply, and expedite the identification of the shortcut actuators by the driver without the driver having to remove his eyes from the road, the shortcut actuators may have a distinct color (that may be illuminated) or use reflective 1 glow in the dark material, shape, size, texture, and/or any combination thereof from other shortcut actuators. The shortcut actuators and their corresponding submenus, options, and/or commands may be arranged in a static order, or dynamic order dependent upon various condition factors. The condition factors may include for example current functions, commands or menu selection factors, driver preferences, temporal factors, environmental factors, traffic factors, preset parental or employer factors, or driver license type factors, or any combination thereof. The disposition of the control clusters can be interchangeable with other control clusters depending on driver preference. The orientation of the control clusters can be changeable depending on driver preference; they may also be rotated clockwise or counterclockwise. The shortcut actuators can be removable and/or interchangeable modules that can be removed from the control cluster and placed in different locations on the control cluster and/or exchanged with other shortcut actuators depending on driver preference and/or vehicle use. The control cluster can also be adjustable in regards to position and/or orientation in relation to the steering wheel to accommodate the driver's preference and driver's physical attributes.

Another possible feature of the invention provides shortcut and/or response actuators having one or more touch sensitive displays with iconic shortcuts for selecting or activating a submenu, function, or driver response. The touch sensitive display lighting intensity and/or color can vary depending on the lighting conditions within the vehicle, driver contact with the touch sensitive display, driver performance or any combination thereof. The touch sensitive display can have two regions; the first region can have one or more shortcut icons and a second region can have a touch sensitive response actuator.

Another possible feature of the invention includes response actuators providing distinct haptic feedback based upon driver responses or selections. The haptic feedback can be distinguishable from other haptic feedback based upon one or more pluses of different amplitudes over different time spans based upon the driver response or selection. The haptic feedback can vary as an inverse of the sequence of the pulse. The haptic feedback is given in a certain order when the thumb gesture is actuated in a certain manner and is given in reverse order when the thumb gesture is actuated in the opposite manner, e.g. right to left vs left to right, clockwise vs, counter clock wise, etc.

The shortcut actuators can include shortcut barriers to prevent accidental selection of the shortcut actuator, for example a 911 emergency shortcut actuator can have a physical perimeter wall around the shortcut actuator rising slightly higher or lower than the actuator to prevent accidental activation of the shortcut actuator by the driver. One or more virtual barriers can separate the shortcut actuators from other component of the control cluster when the control cluster is deployed on a touch sensitive surface; the virtual barriers can be visual and displayed on the touch sensitive display or it can provide distinct haptic feedback when a digit of the driver crosses the virtual barrier, and the haptic feedback can be distinguishable from other haptic feedback based upon one or more pluses of different amplitudes over different time spans. Naturally, both visual, haptic or verbal feedback can be used to let the driver know the position of the thumb. One or more virtual barriers can separate the shortcut actuators from other component of the control cluster; when the control cluster is deployed on a touch sensitive surface: the virtual barriers can provide distinct haptic feedback when a digit of the driver crosses the virtual barrier, and the haptic feedback can be distinguishable from other haptic feedback based upon one or more pluses of different amplitudes over different time spans.

Another aspect of the invention can include the driver's selection and/or activation of shortcut actuators enhancing the reliability of speech and/or gesture recognition by the control system. The possible span of received speech or gesture recognition responses from the driver is reduced and/or narrowed to speech or gesture patterns associated with the selected or activated shortcut actuator.

BRIEF DESCRIPTION OF THE DRAWINGS

FIG. 17A shows a reminder icon in the form of a flag

FIG. 17B shows a fuel level check icon

FIG. 17C shows a set speed icon,

FIG. 17D shows horn icon while

FIG. 17E shows Contact Emergency icon.

FIG. 21A shows Numeric sequences in Seven-Segment and Guided Gesture in Arabic Numerals.

FIG. 21B shows Numeric sequences in Seven-Segment and Guided Gesture in Arabic Numerals with a flow input method.

FIG. 21c shows Numeric sequences in Seven-Segment and Guided Gesture in Indian Numerals.

FIG. 21D shows Numeric sequences in Seven-Segment and Guided Gesture in Indian Numerals with a flow input method.

DETAILED DESCRIPTION OF THE INVENTION

The present invention seeks to improve on the Guided Gesture teachings of commonly owned U.S. Pat. No. 6,731,925 issued on May 4, 2004; the contents of which are hereby expressly entirely incorporated by reference for all purposes. Through the improvements, as described herein, the present invention improves the functionality by introducing shortcut actuators that may directly activate a specific accessory or portable telematics device without the help of an intelligent assistant that uses machine intelligence to select the likely application that is needed by the driver.

This can be achieved without requiring the driver to look down or look away to select the correct shortcut actuator because each shortcut actuator can have a distinct color, shape and tactile feel, and with the use of haptic feedback. Thus, a shortcut actuator can be selected by a driver using peripheral vision and confirmed before activation through a response actuator, via tactile sensing, verbal and visual feedback and during the selection by haptic and tactile feedback that is unique to the shortcut. Furthermore, gestures or responses (gesture and response are interchangeable used) may also be visually represented on or near the shortcut actuator, through the use of a response actuator, so the driver can refer to a standard visual cue when using a function for a long time, particularly when the shortcut visual representation on the controls can be changed dynamically.

The shortcut actuators and response actuators can be physical activated by the driver pushing a button, moving a switch, touching a screen, and/or through speech recognition. For example, the shortcut actuators can be individually actuated by pressure, mechanical, capacitive, resistive, thermal or optical technology and/or they can be actuated in a sequence with a swipe from the right to the left or the left to the right to produce another set of commands that are not related to any of the shortcuts.

Figure 1:
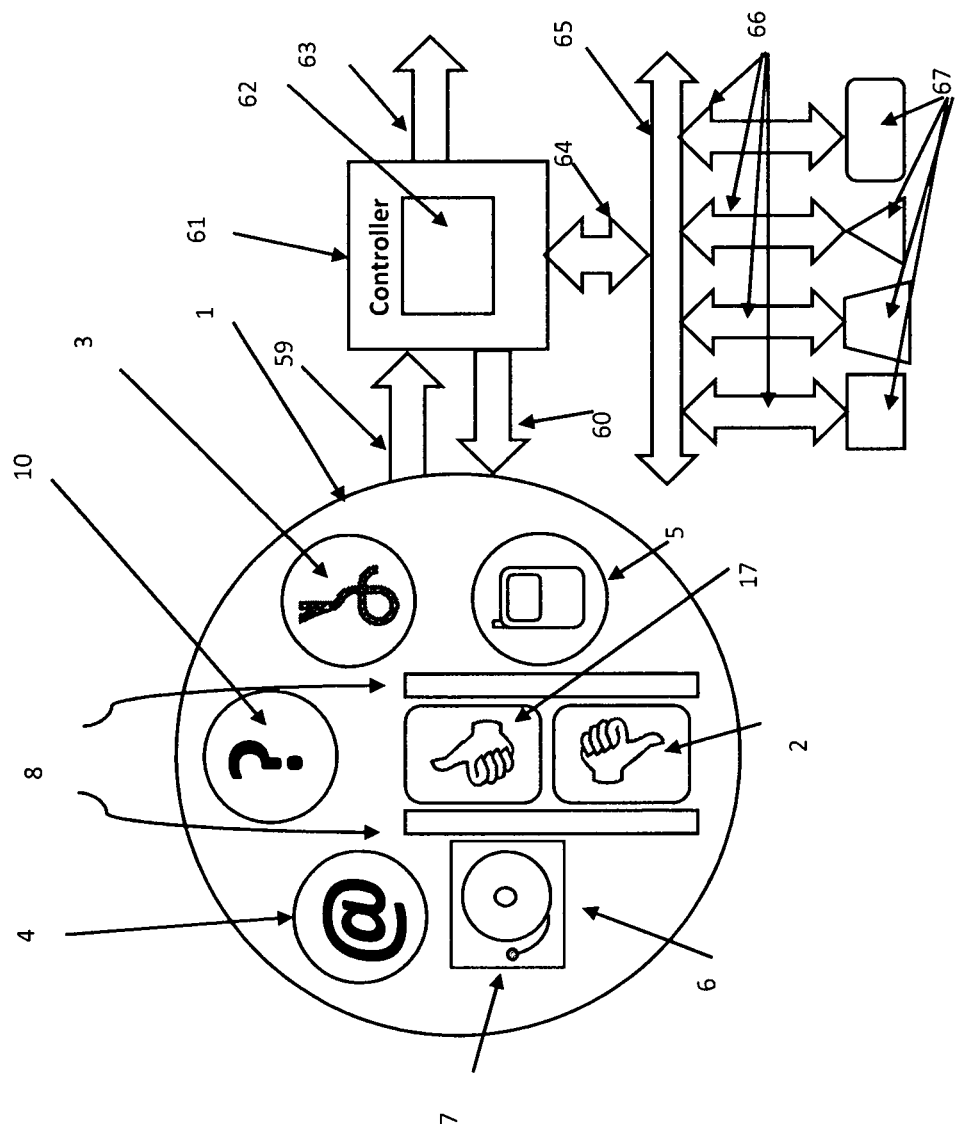
FIG. 1 illustrates an embodiment of a control cluster from a driver's perspective view in communication with a controller, and the controller in communication with a vehicle bus, and the vehicle bus in communication with numerous devices, and two other Control clusters embodiments.
Figure 11:
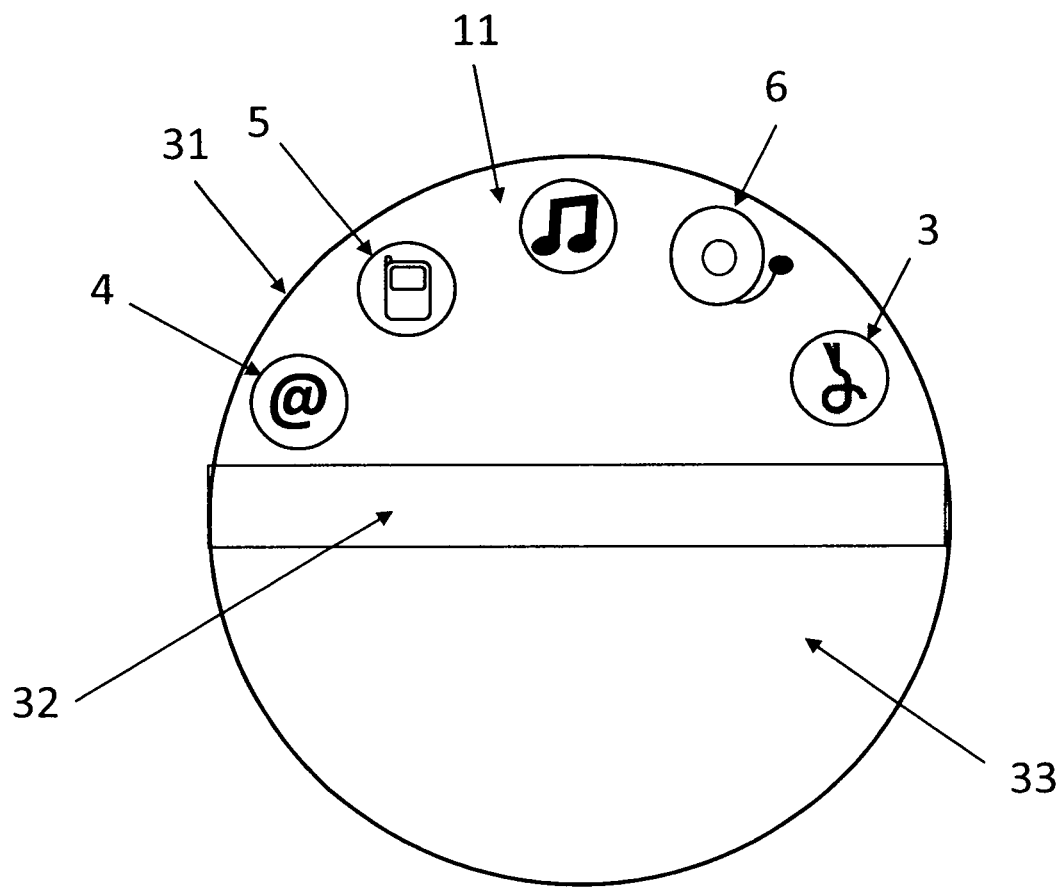
FIG. 11 illustrates an embodiment of a control clusters divided into two regions, the upper region for shortcuts and the lower regions having a touch sensitive response actuator using Thumb Gesture from a driver's perspective view.
Figure 12:
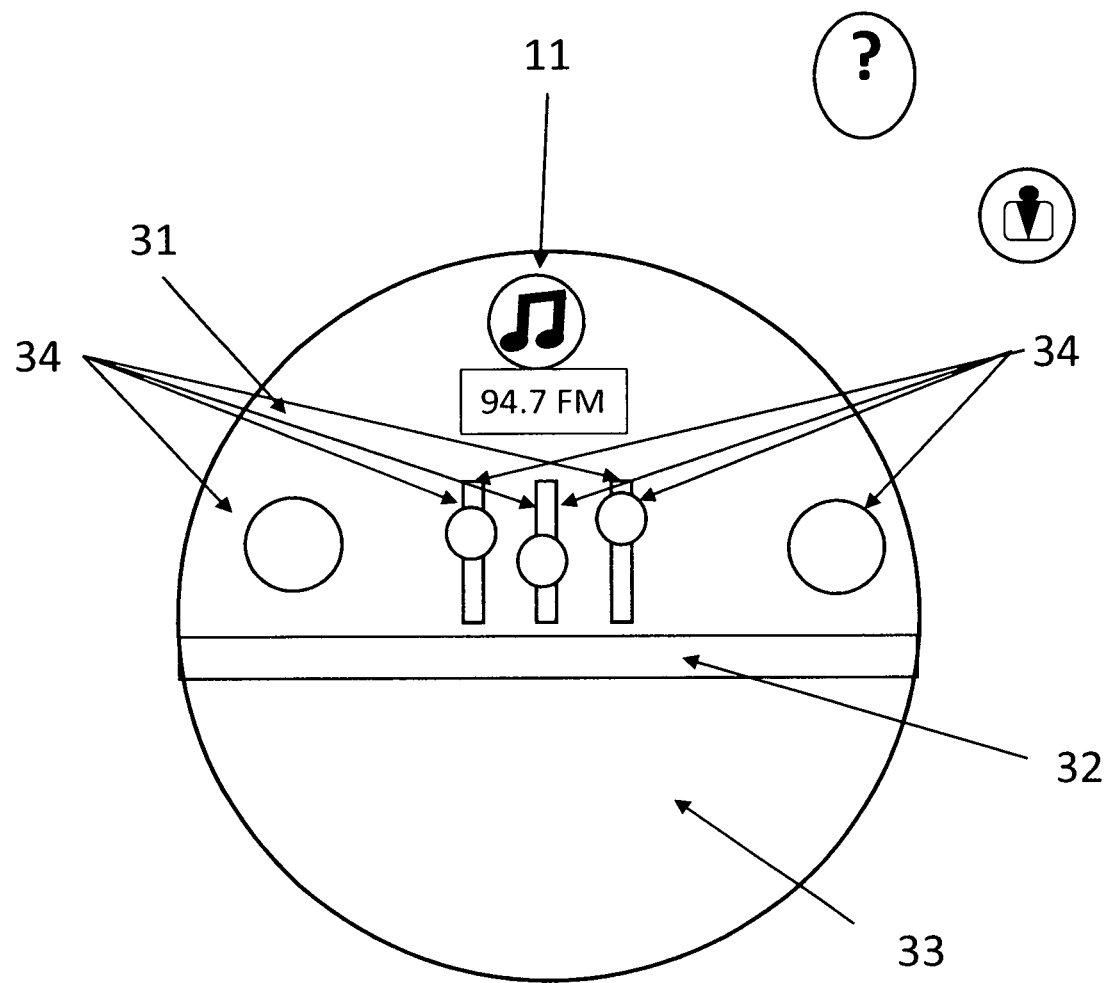
FIG. 12 illustrates an embodiment of a control clusters divided into two regions, the upper region showing an audio submenu and the lower regions having a touch sensitive response actuator from a driver's perspective view.
Figure 13:
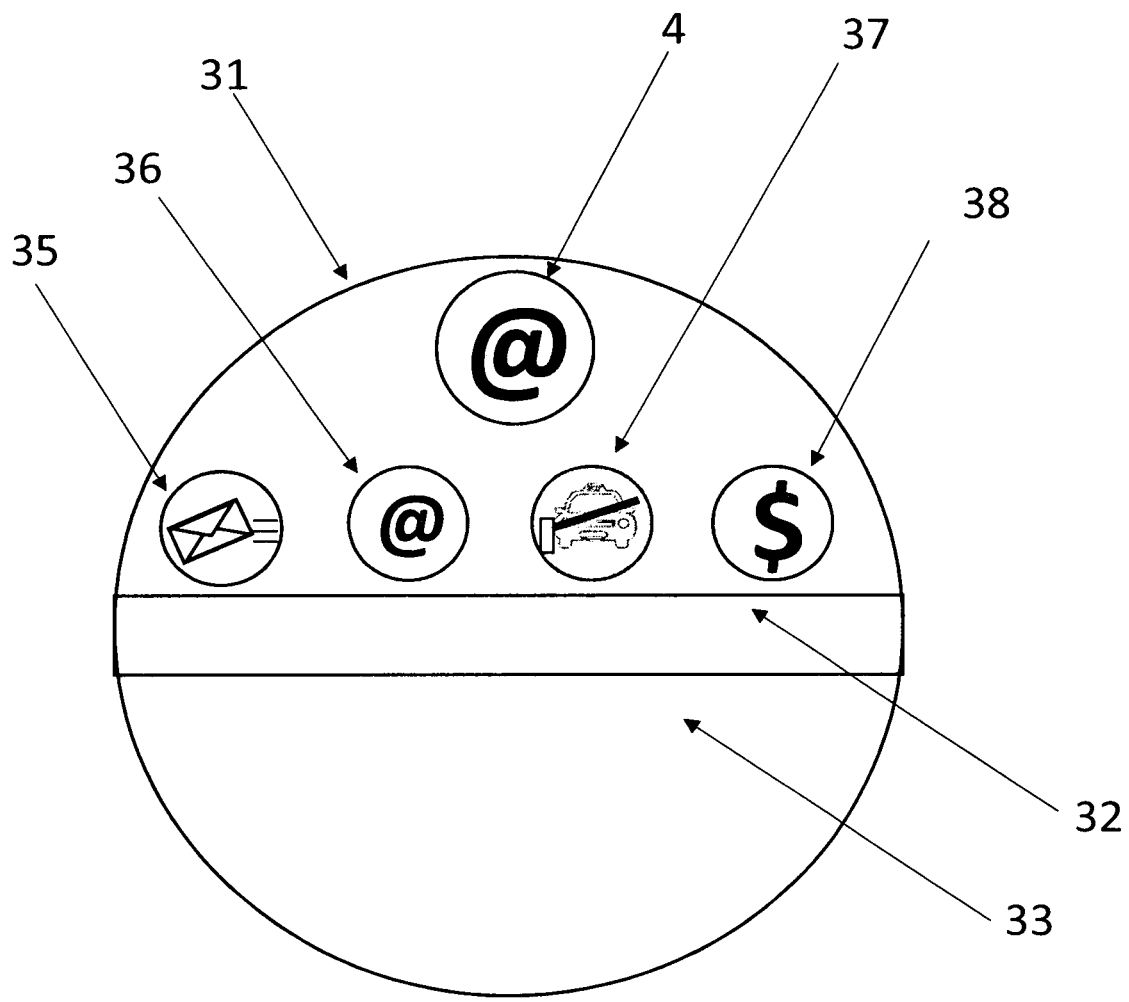
FIG. 13 illustrates an embodiment of a control clusters divided into two regions, the upper region showing a portal submenu and the lower regions having a touch sensitive response actuator from a driver's perspective view.
Figure 14:
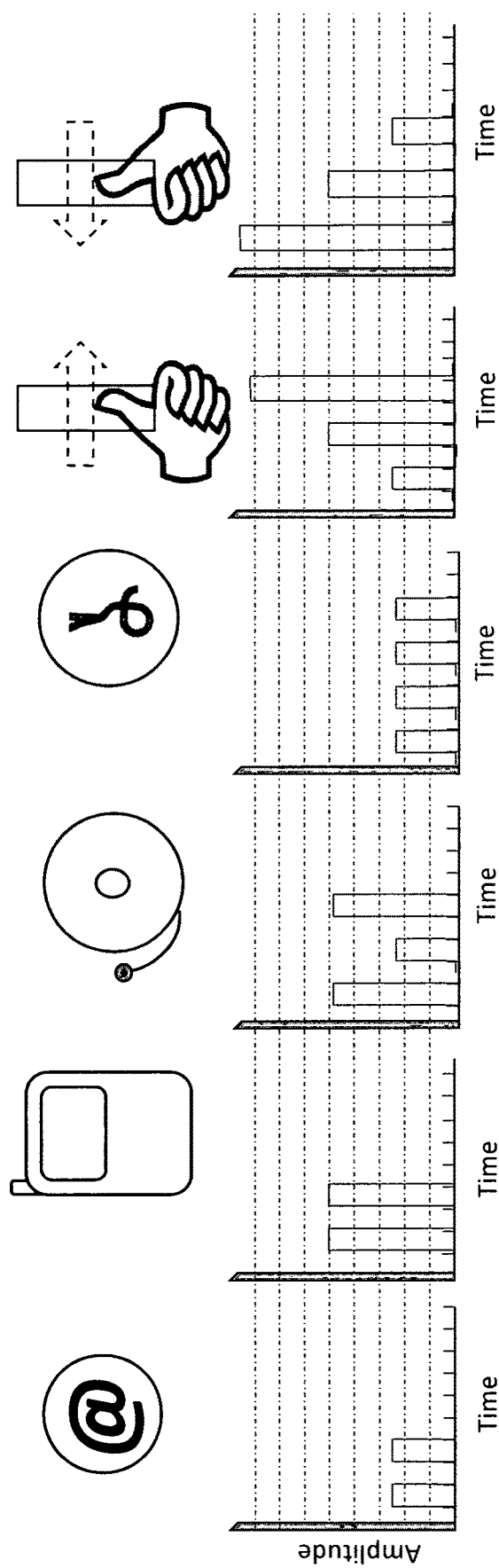
FIG. 14A shows haptic pulse amplitude and duration for accessing e-mail.
FIG. 14B shows haptic pulse amplitude and duration for accessing Phone.
FIG. 14C shows haptic pulse amplitude and duration for accessing Alarm.
FIG. 14D shows haptic pulse amplitude and duration for accessing Navigation.
FIG. 14E shows haptic pulse amplitude and duration for accessing right hand mode gesture
FIG. 14F shows haptic pulse amplitude and duration for accessing left hand mode gesture.
Figure 15:
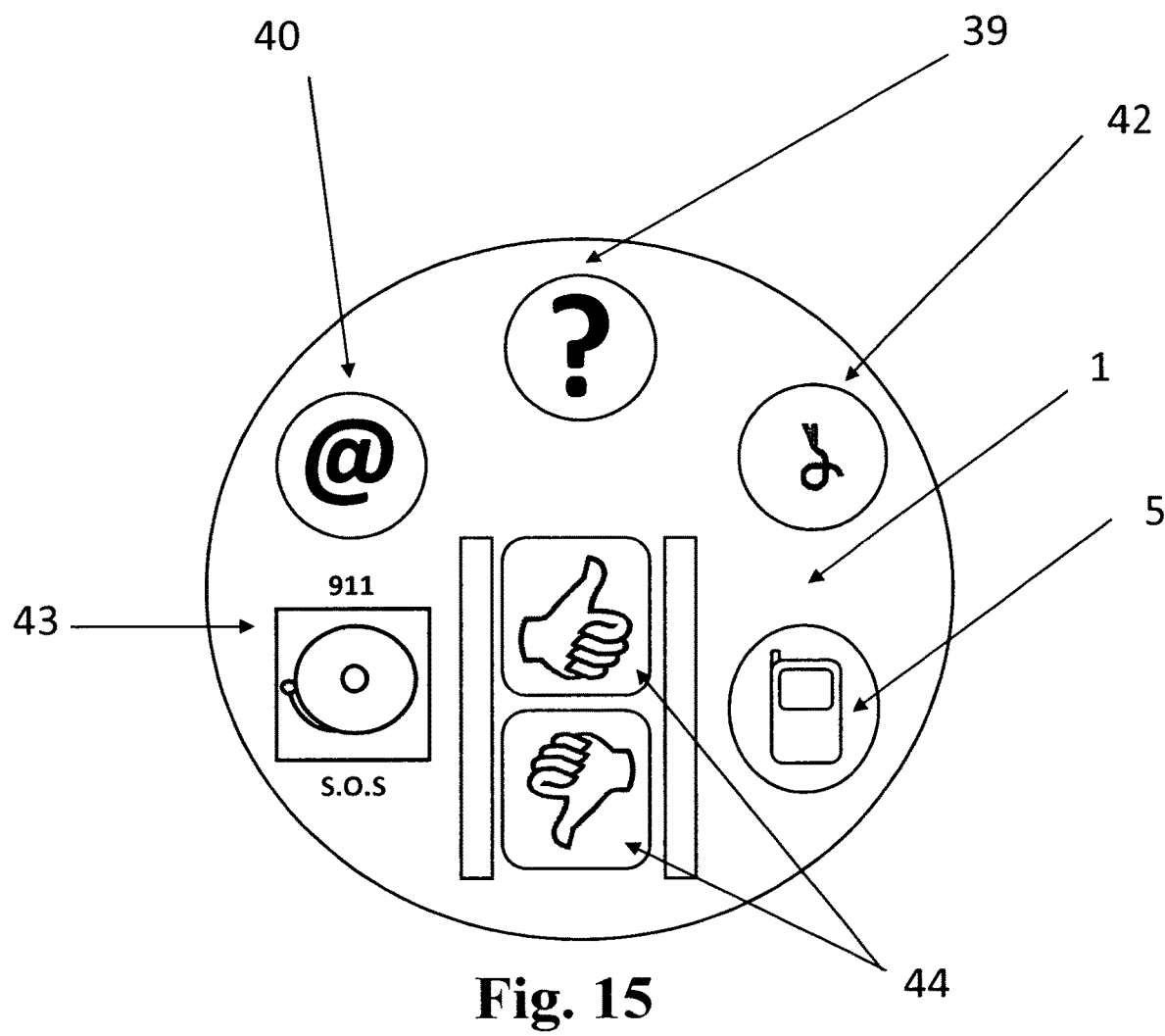
FIG. 15 illustrates an embodiment of a control cluster modularity from a driver's perspective view.

FIG. 1 illustrates an example of a control cluster 1 with various shortcut actuators, including shortcut actuators for navigation 3, portal 4, phone 5, 911 emergency 6, and help 10. The shortcut actuators can be a physical switch that may be activated by pushing the switch or an image on a touch sensitive display 31 (FIGS. 11, 12, 13) activated by touching the image. The number and type of the shortcut actuators is not restricted to the ones depicted in FIG. 1, but are provide for exemplary purposes. Furthermore, the shortcut actuators may include graphics or icons as shown on each shortcut actuator in the figures. These graphics or icons can vary for each individual shortcut type and should not be considered restrictive. The graphics or icons assist in identifying and distinguishing the shortcut actuators from each other; furthermore, differentiation can be achieved by varying color, shape, size, position, texture, or any combination thereof. A shortcut barrier 7 can surround the perimeter of a shortcut actuator and rise above the height of the shortcut actuator to prevent accidental activation of the shortcut. The shortcut barrier 7 can be a physical barrier such as a thin wall. FIG. 1 also shows a response actuator 2 (also referred to as a gesture). The response actuator 2 can include a graphic or icon 14 (FIGS. 3, 4, 5) such as a thumb gesture correlating to a driver's response. A thumbs up icon can be used for yes, while a thumbs down icon can be used for no or cancel. Additionally, a thumb icon pointing to the right may mean "next" or "skip" and a thumb icon pointing to the left may mean "go back" to the previous option. Other gestures include "press and hold" function where the duration of the "press and hold" will call up different functions. One such visual representation can be in the form of white dot which will mean press and hold (e.g. increasing cruise control speed). Another can be a series of smaller dots which will mean multiple presses are needed to effect a range change (e.g. increasing volume, or skip function, etc). The response actuator 2 can be partially or completely surrounded by a back wall 8 to help provide a guide for the driver's digit without the driver having to look directly at the response actuator. Furthermore, the response actuators can be separated from each other by a response actuator separator 17. The shortcut actuator and the response actuator may communicate by at least sending 59 and receiving 60 commands and/or data to and from a controller 61. The controller 61 can communicate commands and/or data 64 from and to a vehicle bus 65.

In one implementation, the invention employs automated machine controls using a controller 61, such as a CPU, an analog or digital circuit, to issue electrical or verbal/visual commands 63 and data 66 to various peripherals and accessories or to portable telematic devices and where the controller's adaptive automated machine logic provides assistance to the driver and optimizes the functionality of telematics features or vehicle function 67 accessibility by arranging them according to a user's needs and preferences based on usage frequency of individual features and/or application or as customized individually by the user preferences, skills and events.

In a CPU based embodiment, the controller is programmable via software 62 and the software functionality is customizable to driver preferences entered directly to the controller or transmitted via wireless means from the web, a portable device, LAN or, WAN or text messages. The controller is responsive to driver actuation entered through the shortcut actuators and/or response actuators and will interpret the driver command based on the preferences as set up by the driver or on a fixed parameters. The gesture part of the command is also interpreted based on preset parameters, taught to the controller as data, to include at least Thumb Gesture, Tap, Press and Hold, Human Language characters and any function specific to the driving purpose. For example, gesturing up while a radio is playing can indicate to the controller that the driver wishes to increase the volume so the controller interprets the gesture and sends command the command through the vehicle bus or through other special communication medium to the radio to turn up the volume a side swipe may mean give us the next station or skip to next track, etc. A Thumb Down command for example, while a phone is ringing, may means Send to Voice Mail. In case of a military application, a soldier using a system may gesture a circle or part of a circle in a clockwise direction. In this case, the controller will interpret this command to mean turn the machine gun mounted on the vehicle clockwise certain amount and will send such command to the controller actuating the machinegun to perform the task. For this latest example, tapping on the sensor reading the gesture will be interpreted as a command to fire in which case the controller will send a command to the controller actuating the machine gun to actually fire the gun. The controller monitoring the control cluster, shortcut actuators and response actuators (also known as thumb gesture capturing sensor) will take the command, interpret through known commands from a memory and then sends the command to the appropriate controller through a communication network or directly to a subject device through physical or wireless bus.

Figure 2A:
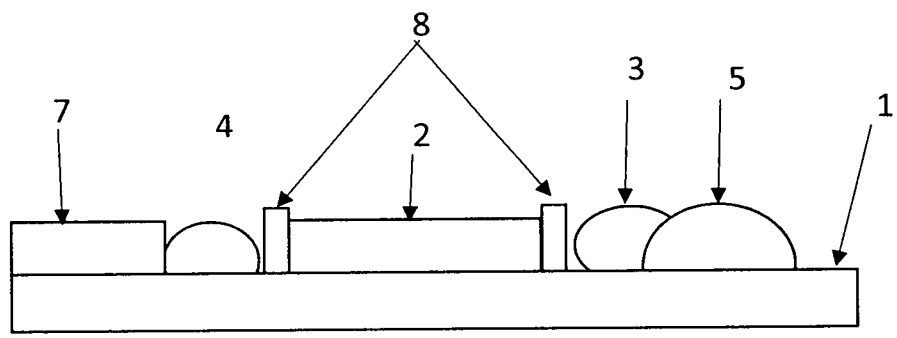
FIG. 2A illustrates a North/12 o'clock view of an embodiment of a control cluster.
Figure 2B:
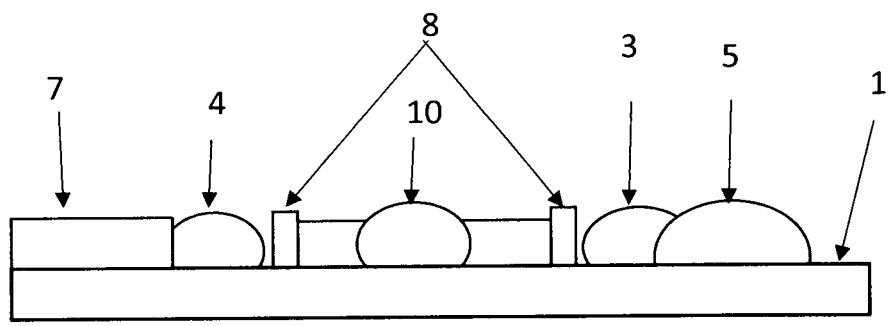
FIG. 2B illustrates a South/6 o'clock views of an embodiment of a control cluster.
Figure 3:
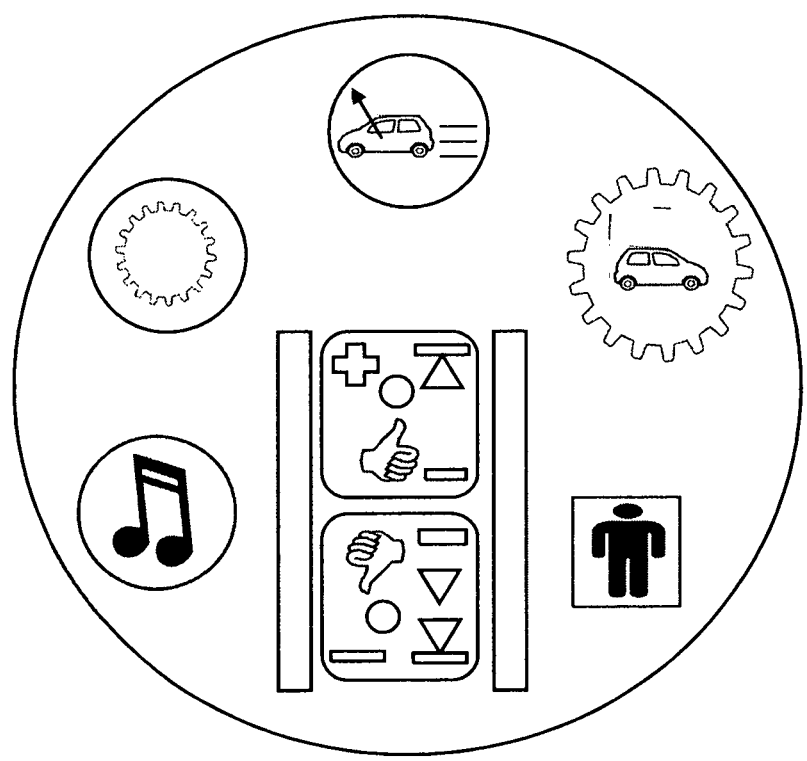
FIG. 3 illustrates an embodiment of a control cluster from a driver's perspective view.
Figure 4:
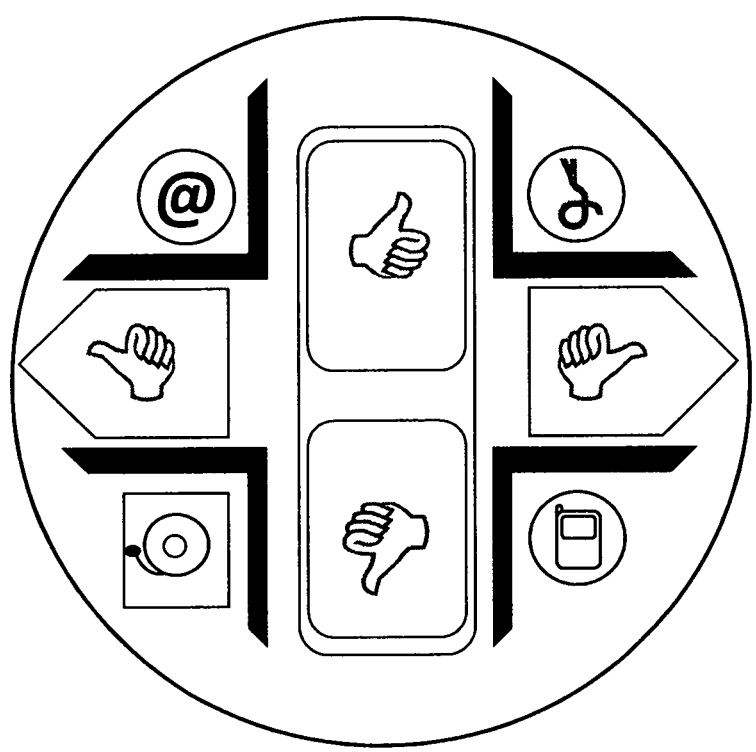
FIG. 4 illustrates an embodiment of a control cluster from a driver's perspective view.
Figure 5:
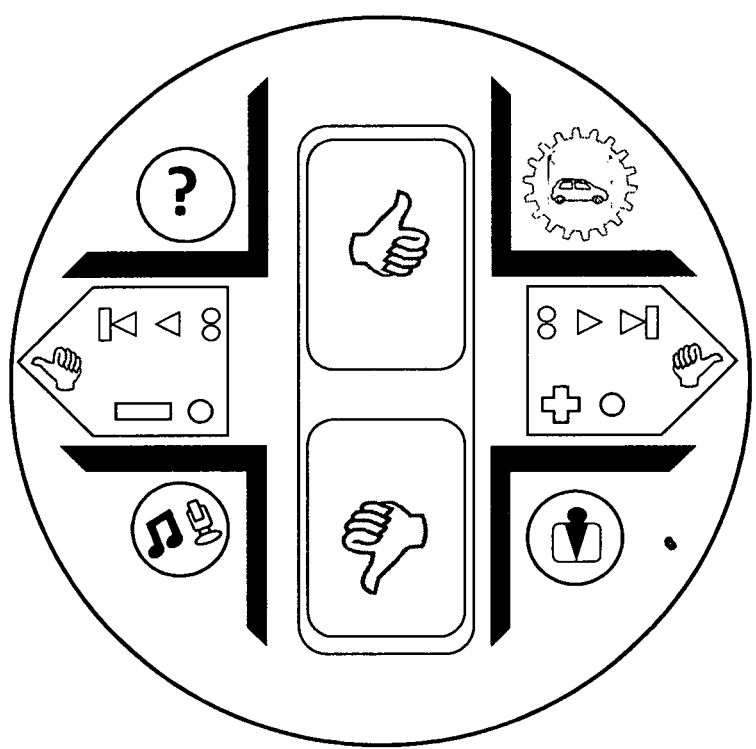
FIG. 5 illustrates an embodiment of a control cluster from a driver's perspective view.

FIG. 2 illustrates an example of a control cluster 1 with views from the bottom and top. Side views of various shortcut actuators, including shortcut actuators for navigation 3, portal 4, phone 5, 911 emergency 6, and help 10. FIG. 3 illustrates an example of a control cluster with shortcut actuators of varying size, shape, color, position and texture. These variances can assistant a driver in identifying a shortcut actuator without having to directly look at the control cluster allowing the driver to maintain his eyes on the road; these shortcut actuators may include actuators for an audio control shortcut (or other entertainment related feature) 11, system setting shortcut actuator 12, concierge shortcut actuator 13, HVAC, environmental or climate control actuators 15, cruise control actuators 16. The response actuator may have additional graphics, icons, or symbols 14 further identify the function response of the response actuator. FIG. 4 illustrates response actuators 2 that include thumb up (e.g. yes), thumb down (e.g. no), thumb to the left (e.g. pervious), and thumb to the right (e.g. next). FIG. 5 includes response actuators with additional graphics such as play, pause, rewind, and fast forward among others.

Figure 16:
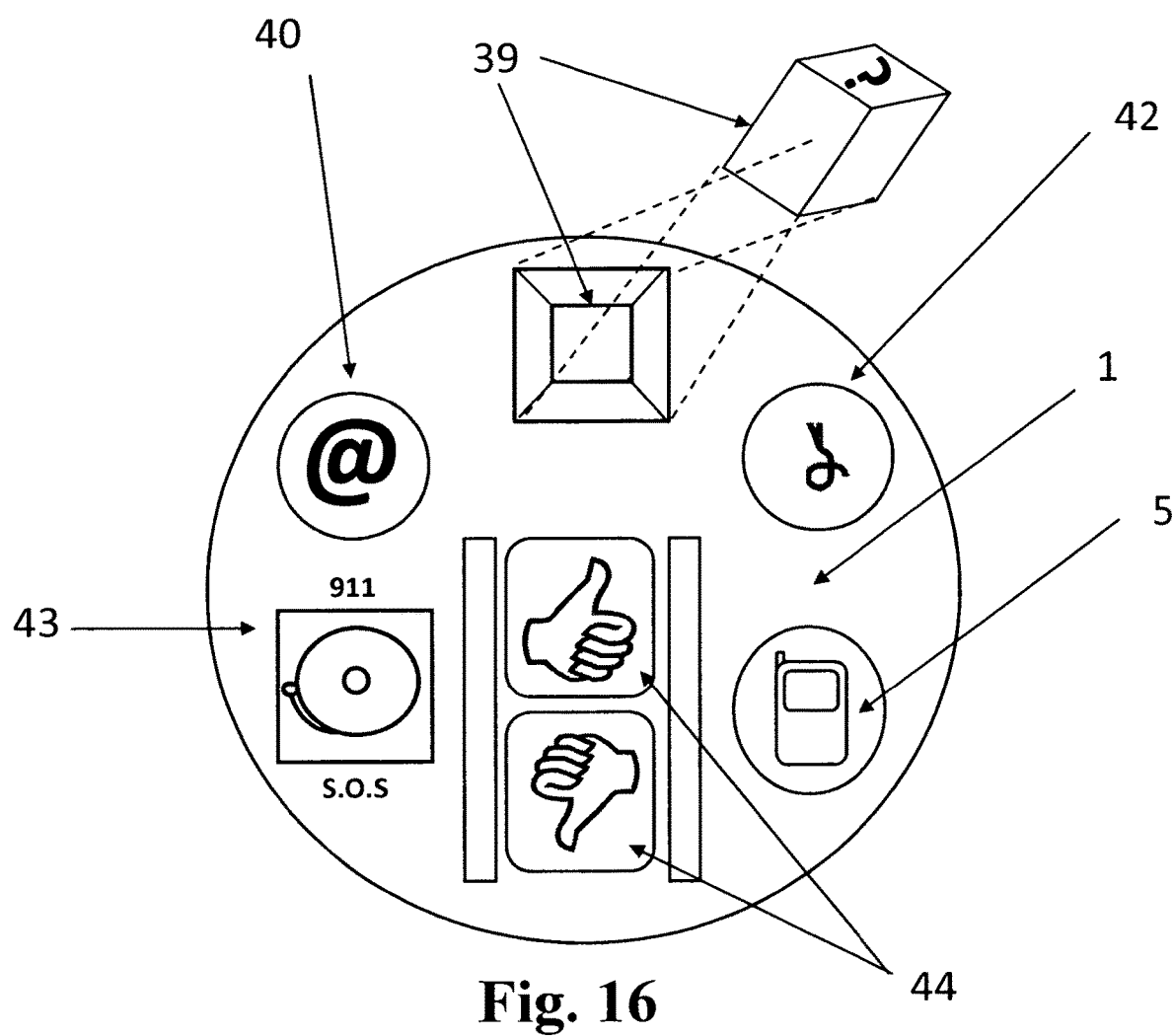
FIG. 16 illustrates an embodiment of a control cluster modularity with a shortcut help actuator connected to a short cut module identifier located behind the shortcut help actuator.

The shortcut actuators for telematics applications, telematics devices, controls or accessories controls can be arranged in a custom topography or layout based upon a driver's preferences and/or physical attributes (e.g. the shortcut actuators can be interchangeable from the right and left side of the control cluster 1 for the convenience of left handed or right handed drivers). For example, a shortcut actuator can be a removable shortcut actuator module, such as help shortcut module actuator 39 in FIG. 16, which can be inserted or removed from a control cluster 1. The control cluster 1 may have one or more shortcut module actuators, such as a portal shortcut module actuator 40, a phone shortcut module actuator 41, a navigation shortcut module actuator 42, and/or a 911/emergency shortcut module actuator 43. The response actuator can also be a response module actuator 44 similar to a shortcut module actuator in that if may be removed or inserted from a control cluster 1. The module capabilities of the shortcut module actuators allow for the shortcut module actuators to be replaced, interchanged and/or exchanged with other shortcut module actuators of different function and/or purpose, including meeting the needs of vehicle designed for specific functions. For example, a vehicle that is being converted from a civilian vehicle to a police vehicle can have a shortcut actuator for a horn exchanged for one for a siren, camera, and/or emergency lights. A police officer can then use the siren and/or emergency lights shortcut actuator to activate and/or control the sirens and/or emergence lights and further control their intensity through use of the response actuator. This feature also makes it easier and more convenient to replace worn and/or defective shortcut actuators and/or to add additional shortcut actuators for new accessories, such as fog lamps for example.

The shortcut module actuators can further include a unique identifier 45 that identifies the type, function and/or purpose of the shortcut actuator to the control cluster. The shortcut actuators can be identified by a controller by the unique identifier and/or through radio-frequency identification where a unique code can be transmitted with each selection and/or command. The controller can recognize the unique signal from each shortcut actuator (wirelessly and/or through wired bus or electrical connection) and will activate the associated component; this can be accomplished without the need to hardwire components.

Figure 6A:
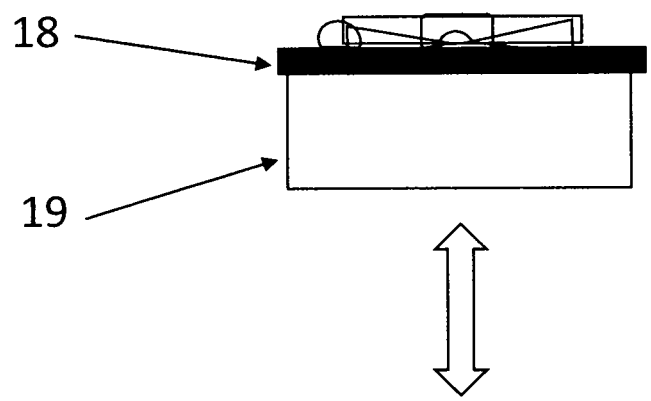
FIG. 6A showing the side view of the control cluster being inserted into or removed from a control dock.
Figure 6B:
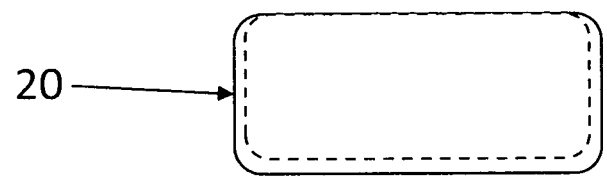
FIG. 6B showing the side view of the control dock as it receives the control cluster.
Figure 7A:
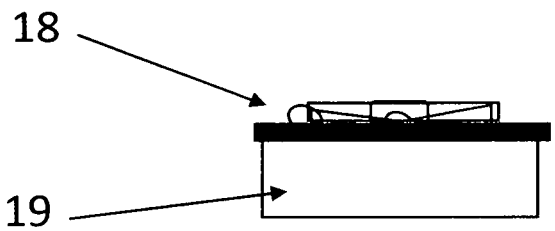
FIG. 7A shows the side view of the control cluster being inserted into the control dock.
Figure 7B:
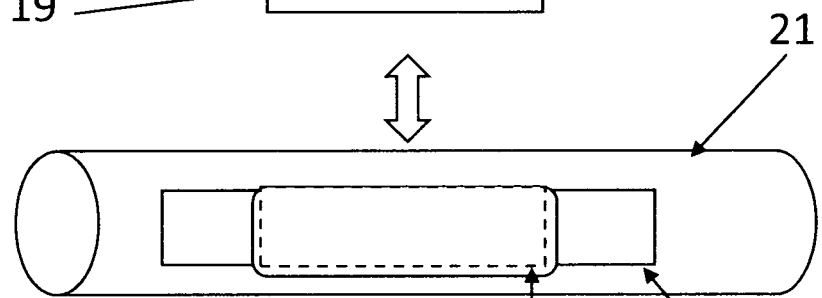
FIG. 7B shows the control dock as attached to a section of the steering wheel.
Figure 7C:
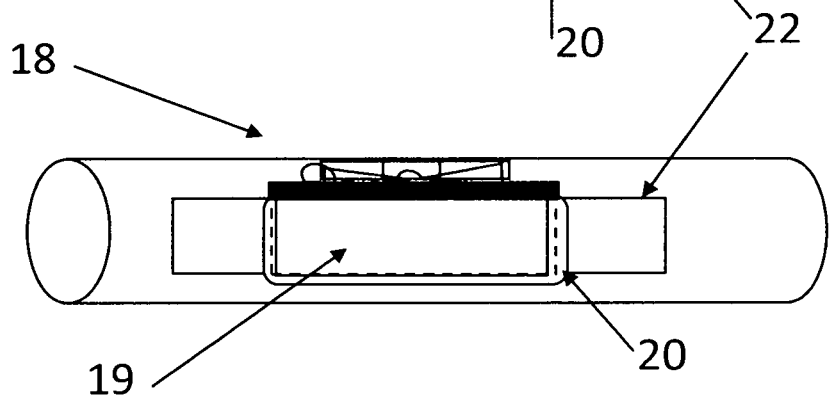
FIG. 7C shows the control cluster after getting inserted into the control dock
Figure 7D:
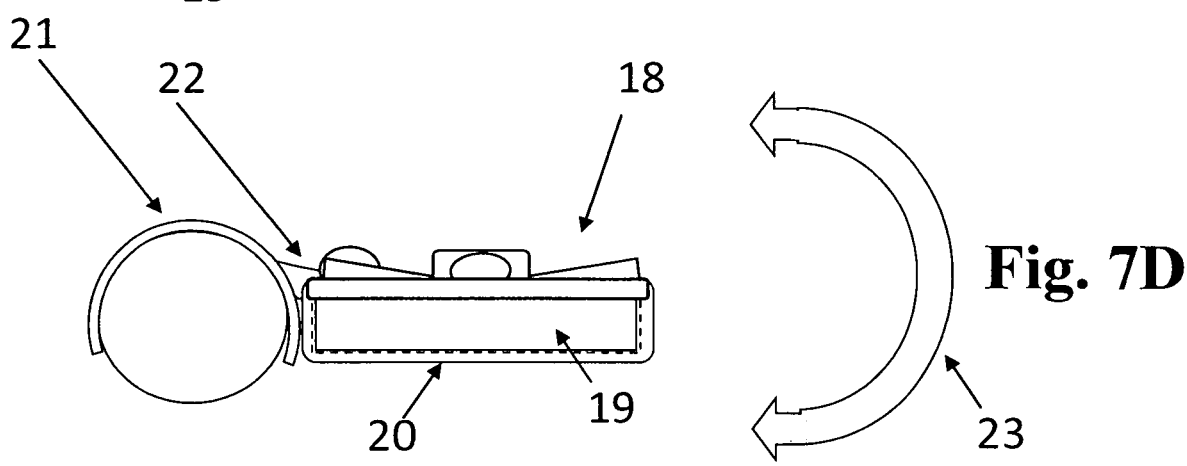
FIG. 7D shows the possible adjustment of the completed assembly with respect to the steering wheel plane.
Figure 9:
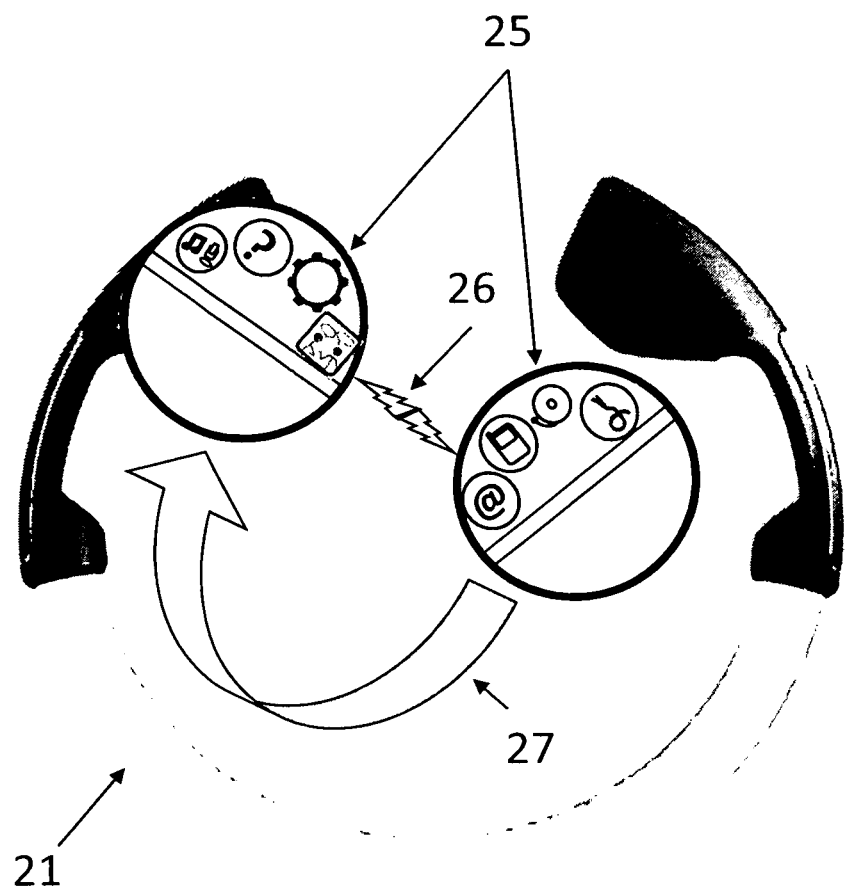
FIG. 9 illustrates an embodiment of a control systems disposed on a vehicle steering wheel from a driver's perspective view where embodiments of a control cluster are shown to interchange.
Figure 10:
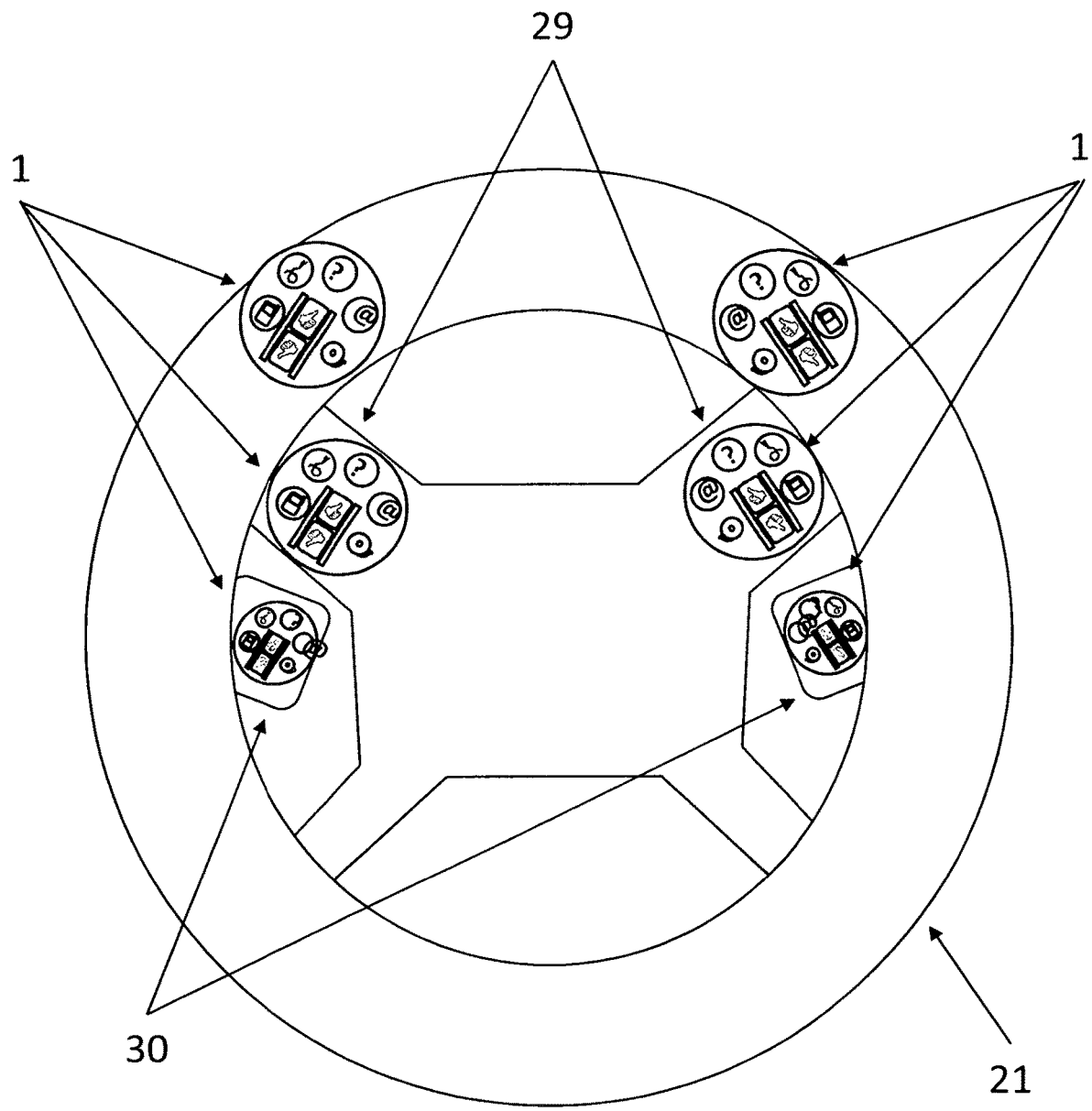
FIG. 10 illustrates an embodiment of control clusters disposed on the upper half portion of a steering wheel/member from a driver's perspective view.

The control clusters can be interchangeable and removable from their respected position on the steering wheel/steering member rim 21 as shown in FIG. 9. The control clusters of FIG. 9 25 can be swapped 27 from left to right based on driver preference and driver physical attributes (e.g. a left handed driver may prefer the control cluster in alternate positions compared to a right handed driver). Swapping control software 26 can adjust the vehicle controls for any such swapping or exchange. In FIGS. 6 and 7, to allow swapping of control cluster module 18, a socket 20 or port for docking a control cluster is provided on the steering member rim 21. The socket 20 is adapted to receive a control cluster module 18 having module control cluster circuitry 19 to facilitate the docking of the control cluster module 18.

Figure 8:
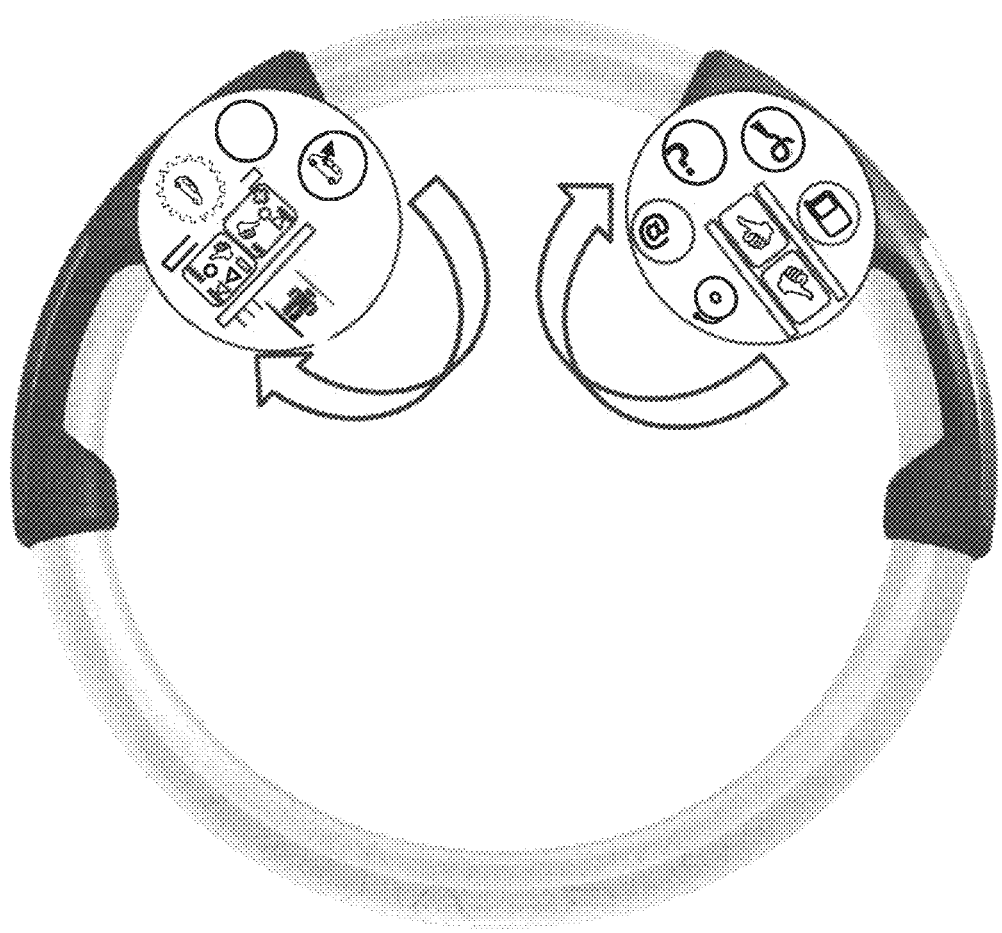
FIG. 8 illustrates an embodiment of a control systems disposed on a vehicle steering wheel from a driver's perspective view where embodiments of a control cluster are shown to rotate.

The control cluster location and/orientation relative to the steering member rim may be adjustable 23 by rotation of the control cluster around the axis of the steering member rim 21 as shown in FIG. 7. A flange 22 can be provided attaching the socket 20 and/or the control cluster to the steering member rim allowing the position and/or orientation of the control cluster relative to the steering member to be adjustable and customizable to accommodate the needs and preferences of individual drivers. This feature can allow for adjustments so that the hands and fingers of a driver are comfortably and properly positioned relative to the location of the control clusters and steering member accommodating the driver's grip of the steering wheel thereby allowing individual drivers to rotate and adjust the control clusters to meet their unique way of griping the steering wheel. This reduces inconveniences arising from trying to reach a shortcut actuator or response actuator because of a driver's digit or thumb length, shape, size, and/or dexterity (which can be severally hindered by arthritis or other medical conditions). In FIG. 8, the control clusters 1 can rotate clockwise and/or counterclockwise 24 relative to the steering member.

In addition to the shortcuts actuators and/or response actuators, the control clusters may include functions to control human-machine interfaces including, speech recognition and/or thumb gesture interpretation sensor to duplicate shortcut actuator functions or sub functions (e.g. increase, decreasing and/or muting volume, rejecting an incoming call, increasing and/or decreasing speed when using cruise control, and/or increasing and/or decreasing distance separating the vehicle from other vehicles when using autonomous cruise control and/or adaptive cruise control systems.

The shortcut actuators can be monitored and can be in communication with a controller that can be adaptive and learning. The controller collects data from monitoring the vehicle, the driver, the environment, the communications, devices, and/or the vehicle computerized controls and driver assistance systems, including the control clusters and can store the data and associate the data with tags relating to events taking place based on one or more of the following: application factors (i.e. the active application, the other applications, their function and their correct operation), portable and embedded Telematics equipment factors (e.g. cellular phone, CB radio, e-mail fax, MP3 player, video player, text messaging, SMS), vehicle accessories and equipment factors (e.g. radio, HVAC, lights, power train), temporal factors (e.g. time of day, day of week, day of month, day of year, etc.), environmental factors (e.g. environmental conditions inside the vehicle, outside the vehicle, traffic, infrastructure type geographical factors including altitude), driver factors (e.g. driver skill factor, driver age factor, driver physiology factor, driver preferences, driver habits, driver licensing, driver traffic record i.e. fines and accidents, driver actions at that instant of time), vehicle factors (e.g. vehicle heading factors, vehicle hearing factors, vehicle posture factors (e.g. forward, reverse, in inclined position, banked), vehicle type, vehicle mechanical status, vehicle maintenance history), and/or regulation factors (e.g. relating to driving, use of communication devices, reporting accident and driving purpose).

The control cluster may include at least one shortcut actuator dedicated for providing help (a help shortcut actuator 10) so that when the shortcut is pressed or the function is triggered, the controller outputs a context sensitive help using as a context at least based on one of the following: application factors (e.g. the active application, the other applications, their function and their correct operation), portable and embedded Telematics equipment factors (e.g. cellular phone, CB radio, e-mail, fax, MP3 player, video player, text messaging, SMS), vehicle accessories and equipment factors (e.g. radio, HVAC, lights, power train), temporal factors (e.g. time of day, day of week, day of month, day of year, etc.), geographical factors (e.g. altitude environmental factor (e.g. inside the vehicle, outside the vehicle, traffic, infrastructure type)), driver factors (e.g. driver skill factors, driver age factors, driver physiology factors, driver preferences, driver habits, driver licensing, driver traffic records (e.g. fines and accidents, driver actions at that instant of time)), vehicle factors (e.g. vehicle heading factors, vehicle bearing factors, vehicle posture factor (e.g. forward, reverse, in inclined position, banked), vehicle type, vehicle mechanical status, vehicle maintenance history) and/or regulations related to driving, use of communication devices, reporting accident and driving purpose.

The controller can maintain a shortcut mode originating from the last shortcut actuator as the default and/or active shortcut selection as long as the driver needs the controller to remain in the shortcut selection. For example, the driver can activate the shortcut actuator for cruise control resulting in the cruising control submenu, functions, selections, and/or commands becoming available for selection through the response actuators. The controller can maintain the shortcut selection as the active shortcut as long as the driver maintains the vehicle In cruise control and/or as the driver desires. However, the controller can yield control to another shortcut actuator and/or submenu, commands, selections as an emerging second condition and/or occurrence arises, such as an emergency action or an incoming call. The driver can respond through the response actuator to the secondary condition with an appropriate action necessary to respond to the condition, such as answering or rejecting the phone call without the need to preselect that needed shortcut actuator (e.g. the phone shortcut actuator). Once the secondary condition has been addresses, the controller will return to the default primary shortcut interface and/or submenu (e.g. the cruise control actuator).

The shortcut actuators can be individual sensors that can vary (e.g. optical-CCD camera, capacitive, resistive, strain gauges and/or mechanical switches). The shortcut actuators can also be icons displayed on a touch sensitive display that can provide unique and distinctive haptic feedback when touched to assist the driver in distinguishing between shortcuts icons and/or letting the driver know when a shortcut has been selected or deselected. The surfaces of the display between the shortcut icons can also provide a haptic feedback ally defining borders and regions so the driver can tell as he swipes his thumb across the surface that he is enter or leaving a region (e.g. shortcut icon region to the response actuator region (i.e. thumb gesture interpretation region), of the display without having to look at the display. Crossing the boundary from the shortcuts icons region to the response actuator region can provide a different haptic feedback from crossing the response actuator region to the shortcut icons region.

The touch sensitive display can change from displaying the initial shortcuts actuator to displaying the submenus for the activated shortcut icon in a visually distinctive (e.g. color, lighting intensify, and/or shape) manner. The touch sensitive displays can be swappable physically or can be selected to swap their function through a setting shortcut option. The touch sensitive displays located at the on the upper half of the steering member including the spokes, the rim or special flag extended from the rim or the spoke of the steering wheel and can be easily recognizable by the driver's peripheral vision. The steering wheel can include displays connected to cameras showing the various sides of the vehicle as selected by the driver for changing lanes, reversing, parking and/or stopping at the proper locations. The display can show the requested view based on turn signal activation, reverse or forward gear selection, and/or when directly selecting such view by the driver from a shortcut actuator. The touch sensitive displays may also include control icons simulating button, knobs, levers, joy stick or other controls to be touched activated by the driver like the physical control would be controlled.

The controller can monitor the touch sensitive displays located at the on the upper half of the steering member including the spokes, the rim or special flag extended from the rim or the spoke of the steering wheel and are easily recognizable by the driver's peripheral vision. The controller can access a database (remote or on board) and retrieve photos of an end destination (e.g. house, establishment, or POI) to aid the driver in finding them.

The controller can confirm the driver's selection verbally, visually, or through haptic feedback so the driver is certain that the desired function was selected. The verbal confirmation can be verbal, a beep (preferably a distinct one), or a display of the shortcut selected on a display visible while the driver's eyes are on the road or by changing the color or shape or aura of the shortcut actuator (or the lighting of the vehicle cabin) so it is easily visible through peripheral vision of the driver, showing that it was selected.

It should be appreciated that the features of the steering wheel vehicle control system may be interchanged between each other or otherwise used to form yet additional configurations.

The Guided Gesture Sensor

In our prior disclosures, we proposed a Thumb Gesture as a mean to input data into a controller to control a menu, a vehicle accessory or a function or a vehicle or portable telematics device. The type of Thumb Gesture introduced was centered around electromechanical sensors, including a modified rocker switch, or modified slide switch, thumb wheel or jog wheel. The other type of Thumb Gesture sensors that were introduced was a touch sensitive (capacitive, resistive, thermal or pressure sensitive as well as optical sensors). These sensors where arranged as a cluster or a continuous surface. That was a breakthrough in designating a control that is not dependent on present physical limitation, but it also introduced a commonly experienced problem with pattern recognition and it is the issue of reliability based on the quality of input supplied by the user. In the provisional patent 61/446,179, we specified a Guided Gesture where the gesture is done through a tactilely sensed track or an embossment so a driver can input present pattern without the errors associated with entering free form gestures. Referenced U.S. Pat. Nos. 4,199,751, 5,521,986, 6,326,947 and 7,729,542 used a straight forward inverse encoding of a Seven-Segment encoding. As a background information, Seven-segment display (SSD), or seven-segment indicator, is a form of electronic display device for displaying decimal numerals that is an alternative to the more complex dot-matrix displays. Seven-segment displays are widely used in digital clocks, electronic meters, and other electronic devices for displaying numerical information: Although the sensor embodiment can be of any of these representations.

Figures 18A, 18B:
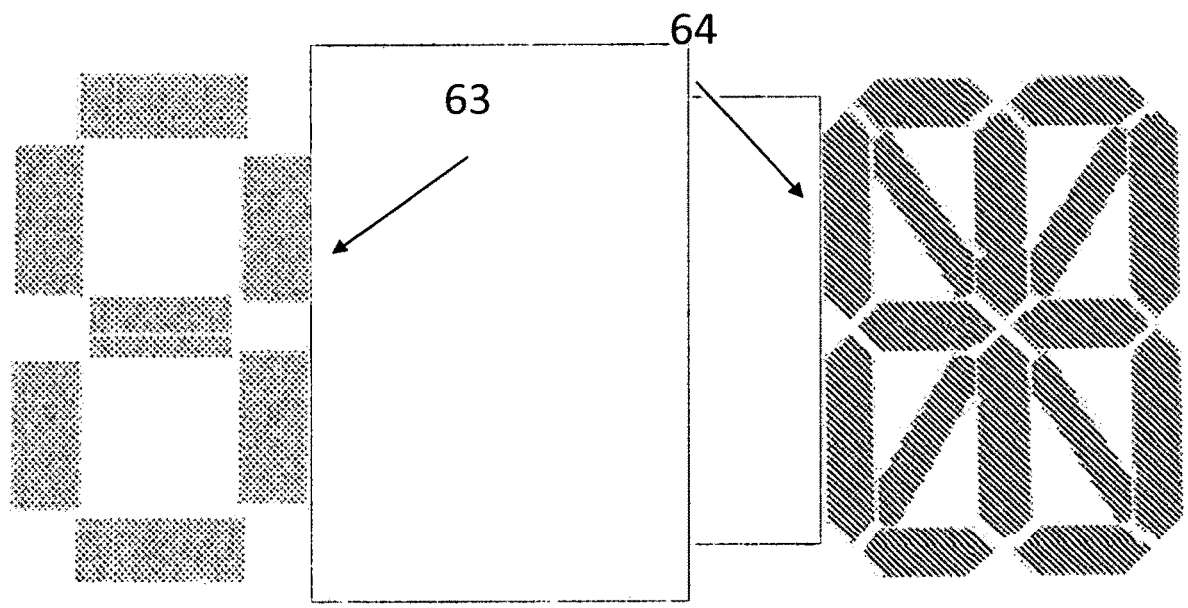
FIG. 18A displays standard Seven-segment sensor
FIG. 18B displays Fourteen-Segment sensor.

The Seven-segment shaped sensors proposed by the referenced patents require seven distinct sensors to be individually activated by the driver. FIG. 18, 63 and 64 shows such a sensor cluster (Seven-segment and Fourteen-segment sensor and the segment that need to be pressed to use them to produce each English alphabet (English is used here for example only and this invention is not limited to just English). None of the referenced patents suggest that such system can be used by a vehicle and the reason is the amount of work required to do such entry. Other patents introduced what is literally a foreign language, i.e. a new way to write an alphabet in a manner that is not at all related to the alphabet as visually recognized by a reader.

Figures 19A, 19B:
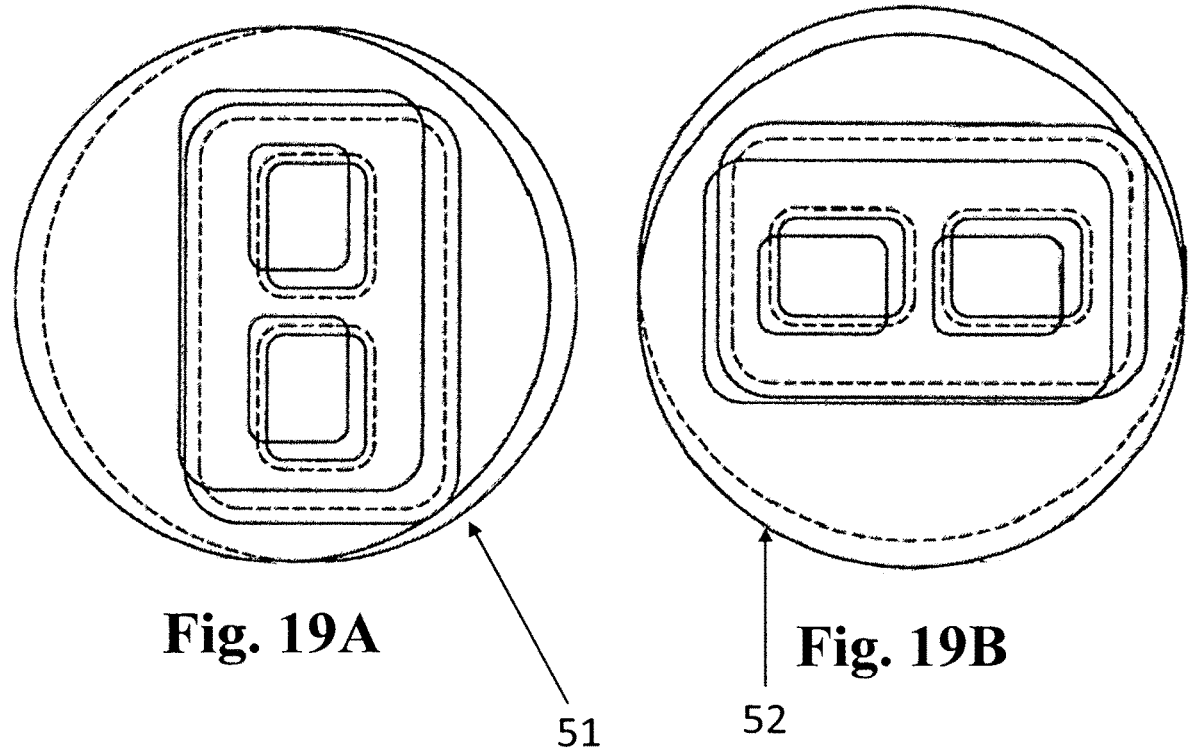
FIG. 19A shows Guided Gesture sensor for a Latin alphabet.
FIG. 19B shows Guided Gesture sensor using Seven-segment template oriented for Arabic.
Figure 20A:
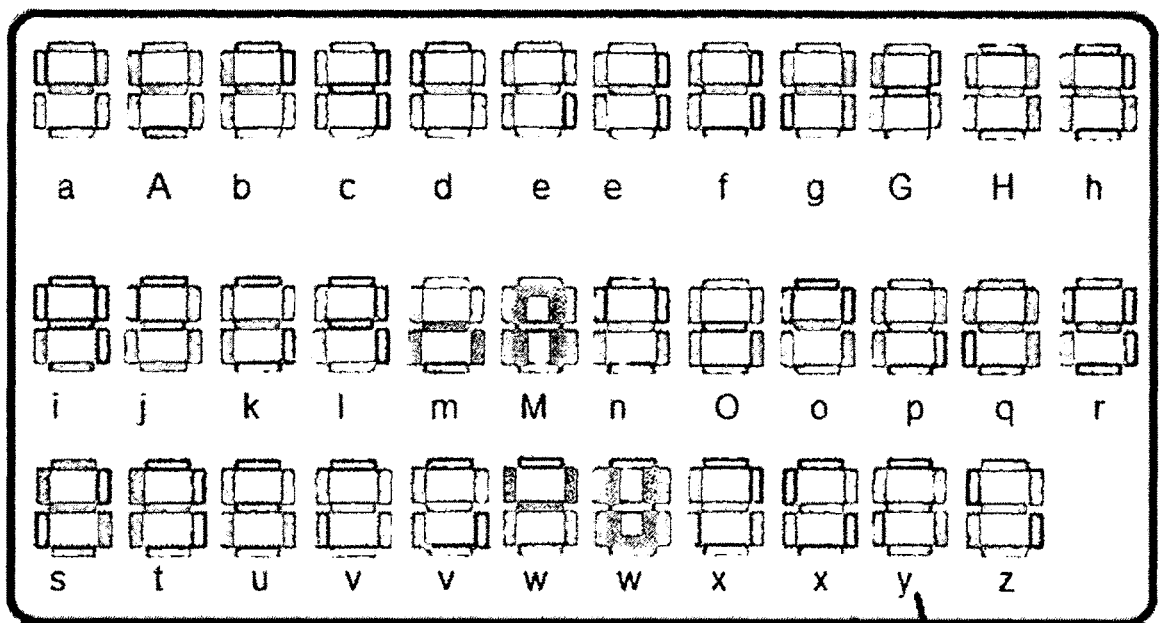
FIG. 20A shows segmented character as individual segment input sensor.
Figure 20B:
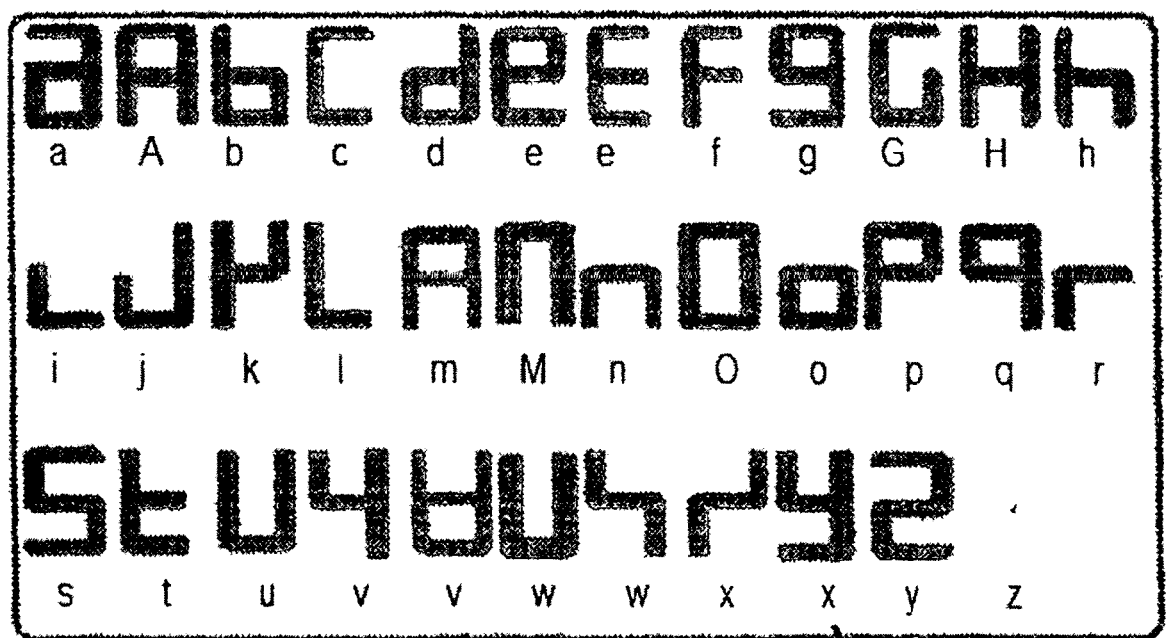
FIG. 20B shows segmented character input sensor with a flow input method.
Figure 22:
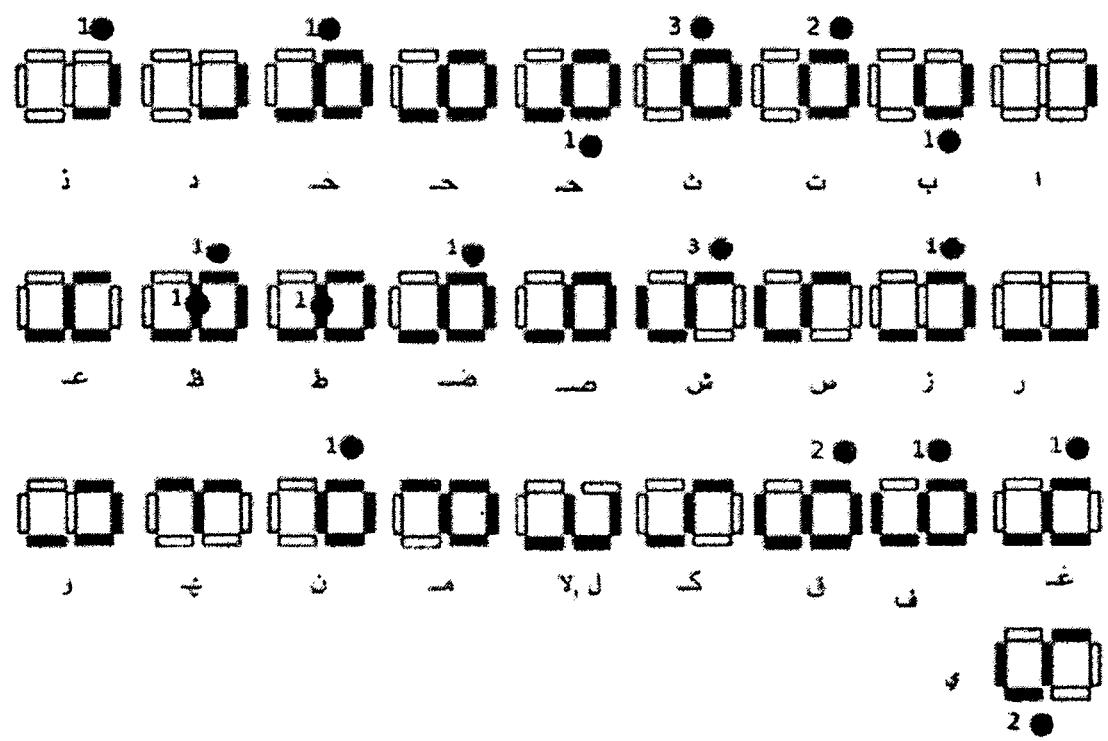
FIG. 22 shows Arabic Alphabet sequences in Seven-Segment.
Figure 23:
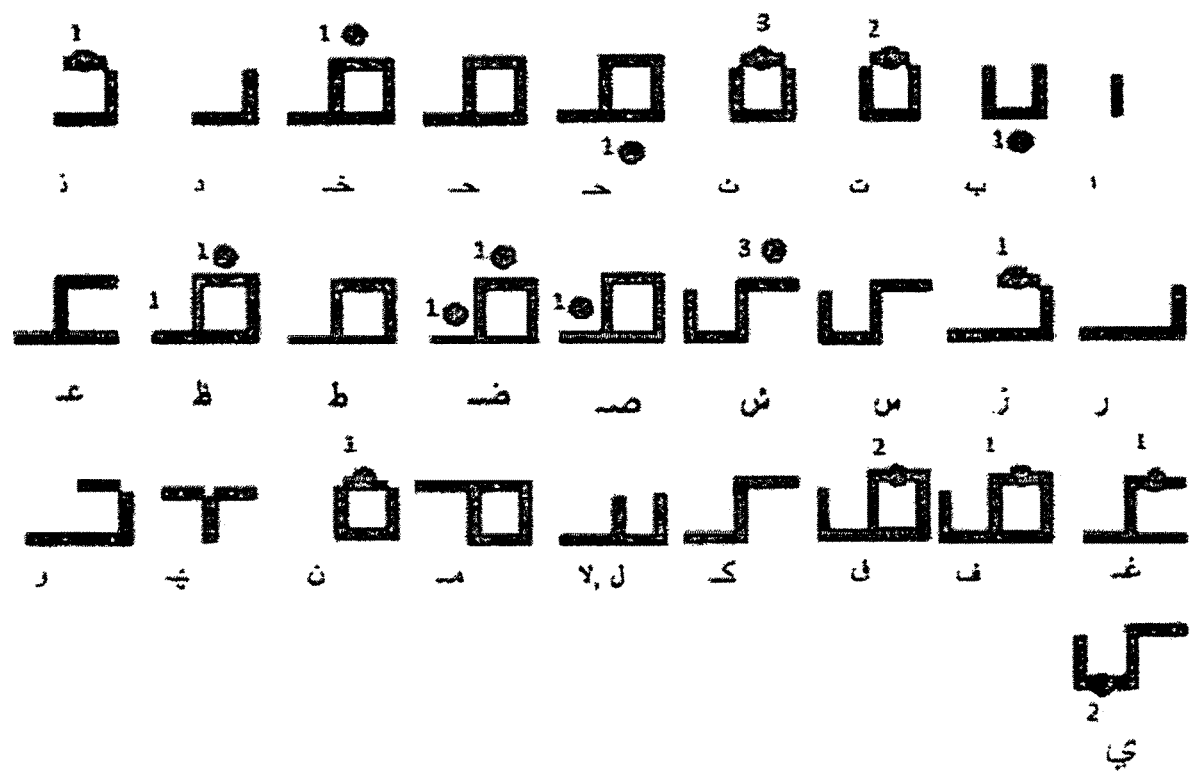
FIG. 23 shows Arabic Alphabet in Guided Gesture with a flow input method.

The Template described allows a driver to run their thumb along a groove that is shaped like an alphabet they recognize thus creating a smooth flow of a character that is more like doodling and does not require the driver to look to see which sensor to actuate next. FIG. 20, 74 shows the tracked alphabet as it will be felt by the driver thumb as he literally paints the character with his thumb or digit. FIG. 21, 75-76-77 and 78 show how the same template with the same orientation can also create Arabic Numerals as used in the west and Indian Numerals as used in Arabic speaking country. Changing the template a driver can enter Cyrillic characters, Sanskrit characters or other Alphabetic character, including Katakana and Hiragana. In a further proof of the system flexibility, changing the orientation of the Guided Gesture Template, FIG. 19, 51 to FIG. 19, 52, will allow for Arabic alphabets to be entered, and again, the comparison with the same alphabet entered using Seven-segment encoder Vs the Guided Gesture shows the amount of sensor actuation needed while the Guided Gesture output is shown as a continuous flow that can be done without the multiple selection and multiple eyes off the road required by the referenced patents. Trying to swipe among the Seven-segment arrangement without looking will add to the cognitive load of the driver as they will have to count the number of sensors covered vs. feeling the continuous flow of the sure gesture. FIG. 20, 73 shows the number of segments that must be actuated to complete each alphabet FIG. 20, 74 shows the Guided Gesture flow using the template.

Figure 24:
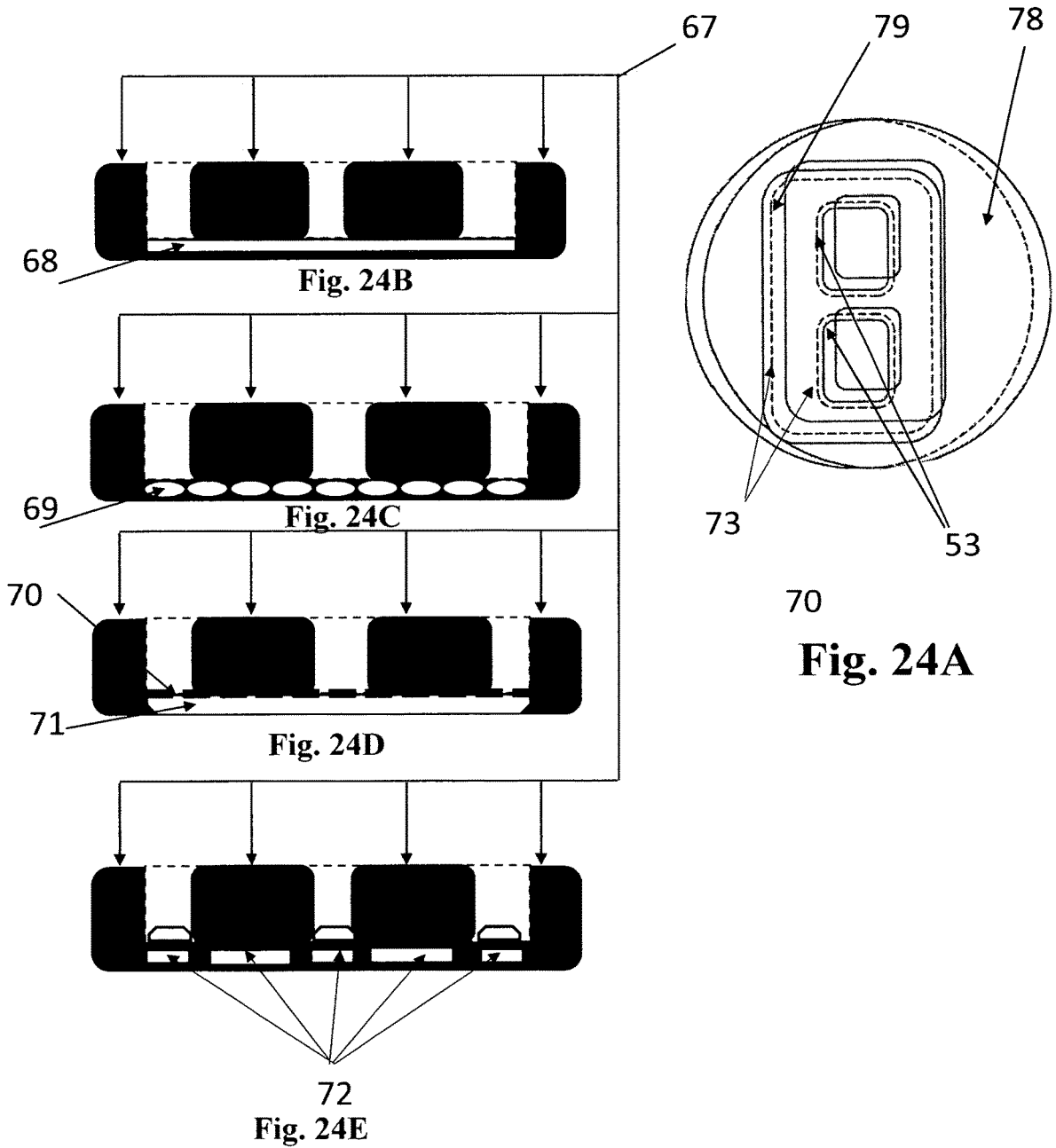
FIG. 24A shows Guided Gesture sensors and template.
FIG. 24B shows Capacitive or Resistive Guided Gesture sensors and template.
FIG. 24C shows discrete optical or field type Guided Gesture sensors and template.
FIG. 24D shows CCD camera Guided Gesture sensors and template.
FIG. 24E shows conductive electrodes Guided Gesture sensors and template.

The new sensor is best embodied in two pieces, a template FIG. 24, 51 that is replaceable for each type of driving application, driver preferences, language etc. The template has surface with a hole shaped like a rectangle FIG. 24, 79 with rounded edges and FIG. 24, 53 showing two islands with two islands shaped like a rectangle with rounded edges, disposed independently in the middle of the islands and equally spaced to overlays a sensor FIG. 24, 68 (a capacitive or resistive, pressure or thermal sensor actuated by touch) FIG. 24, 69 (discrete optical or field type sensor where a touch is not necessary to register an electric signal), e.g. FIG. 24, 71 (a CCD camera with image processing software FIG. 1, 62 residing in the controller FIG. 1, 61 and FIG. 24, 72 using discrete sensor located on a lower shelf than the template bottom and FIG. 24, 73 where conductive electrodes with at least a magnetic field, capacitive field or a resistive field detect a finger being traced while touching an island and the wall of the square hole.

The sensors will detect a Guided Track using the technologies of the respective embodiments and send the information to the controller, 61 to be processed by the software and then send the gesture interpretation over the vehicle bus or another communication protocol to the peripheral 67. The trace over the groove will produce over the groove; pass the information to a controller with a program and memory that will compare the sensor data to the stored data and sends the interpreted commands and send it via a network to be handled by the subject peripheral or device controllers.

The software FIG. 1, 62 used in the controller, 1-61 used in The sensors in embodiment 68, 69 and 70, may end up being in touch with the islands or may detect the islands because of the way the template is constructed or because the sensors are configured to be a one large grid. Also, in case of the embodiment using a CCD camera, FIG. 24, 70. The camera will pick up the bases of the islands in the captured image. To eliminate a false reading, the controller. FIG. 1, 61 and the software. FIG. 1, 62 will filter out the patterns generated by a template by presenting the software to know what template is being used. Alternately, adaptive learning software will detect all forms that come in contact with the field of detection by the sensor and will then eliminate the "never changing pattern" data, e.g. the islands in FIG. 24, 53 and will only analyze the data generated by the changing field of detection.

In addition to filtering out unwanted data, the software FIG. 1, 61 will also have to detect the correct character. In case the gesture is not recognized, the software will send a command to the controller that can activate a haptic pattern indicating error, a verbal, audible or a visual error message will also be given to the driver. If the gesture traced by the driver is recognized by the software, the software will send the information to the intended source.

In other functionality, the software FIG. 1, 62, will also recognize other gestures as in gestures used to switch between alphabet FIG. 20, 74 and. Numerals, FIG. 21.76. This can be done by having a routine to recognize a swipe across the certain parts of the template tracks to one side which switches to numerals and swiping across the template fact to the other side will switch back to alphabet. Similarly, a swipe between certain tracks can change the output between Caps and Lower case and back when another swipe is performed.

In another functionality, where a text is actually being entered into a data field, e.g. a police officer in car terminal, the software will communicate with the database, understand what field is needed and switch to such field automatically. Similarly, the software will recognize proper names (either from the data base being populated by the police officer, as an example, or from a built in learning dictionary) and capitalize them. The software also will recognize the beginning of the line and will capitalize the text automatically.

The main function of the software will of course be entering a character. The recognition of the character is not dependent on character recognition so no massive computing or algorithms are necessary. When the system get a combination of tracing that amount to a character, the system will inform the driver via the aforementioned output means of the character and the driver can automatically begin to enter the next character. The system may also accommodate slow gestures from people with physical limitation or novices and allows for a command gesture to be issued that is equivalent to a writer moving the hand to enter the next character. The gesture may be in the steering member under the grip of the driver, etc.

In some cases, the character may be a sub character or incomplete unless an accent, an umlaut or similar making is added. For example, U and 0 with Umlaut. Share the U in common and if the driver is slow in entering the Umlaut or the system is not equipped to handle the specific character because the original template is English, but the driver needs to enter a German word, the system will pause and return and wait for the Umlaut to be entered if the driver kept gesturing even after a character is already detected.

the controller is programmable to predict the character being entered as swipes are being carried out. The controller will use context based previous character or characters imputed at the current operation or the words entered during the current operation or based on driver previous data entry, time of day, day of week, day of year, active application and so forth.

The driver gets visual or audible feedback about the predicted before it is completed. If the driver continues to enter the character the prediction is automatically dismissed and the controller will continue to monitor the character entry and make the next prediction or wait for the driver to stop the swiping to process the information entered.

another switching method between alphabet and numerals can take place based on the type of date being entered. For example, when entering a street number into a navigation device, the controller will recognize the field a numeric and will accept the data as numeric and when the field is looking for a street name, the controller will switch to recognizing alphabet without the need for a manual mode change by the driver.

location while the driver s in the vehicle. As a result, the phone and/or the MP3 player end up in the cup holder, on the driver lap, on the passenger seat or in the armrest storage which add to the risk of falling while driving or the driver having to take eyes off the road to reach and use the phone while driving, particularly if they are trying to find out who is calling. As evident from the table below, Table 1.0, locating/reaching/answering hand-held device is the second highest complex secondary task a driver can engage in while driving. Having the devices lying around unprotected will make it likely that they will fall from the seat/cup holder which will lead to more increased risk of distraction and accidents. Furthermore, in event of an accident, the cell phone may get damaged beyond usability so the driver is left without a method to call for help. [0086] The problem is then, real and quantifiable and warrants a serious solution.

TABLE 1

Table 2.1 Assignment of secondary tasks into three levels of manual/visual complexity.

| Simple Secondary Tasks | Moderate Secondary Tasks | Complex Secondary Tasks |
| --- | --- | --- |
| 1. Adjusting radio | 1. Talking/listening to hand-held device | 1. Dialing a hand-held device |
| 2. Adjusting other devices integral to the vehicle | 2. Hand-held device-other | 2. Locating/reaching/answering hand-held device |
| 3. Talking to passenger in adjacent seat | 3. Inserting/retrieving CD | 3. Operating a PDA |
| 4. Talking/Singing: No passenger present | 4. Inserting/retrieving cassette | 4. Viewing a PDA |
| 5. Drinking | 5. Reaching for object (not hand-held device) | 5. Reading |
| 6. Smoking | 6. Combing or fixing hair | 6. Animal/object in vehicle |
| 7. Lost in Thought | 7. Other personal hygiene | 7. Reaching for a moving object |
| 8. Other | 8. Eating | 8. Insect in vehicle |
| | 9. Looking at external object | 9. Applying makeup |

The driver gets visual or audible feedback about the character entered once completed or if predicted before it is completed. The driver will also get an audible or a haptic feed back in case the character entry did not result in a recognizable character.

The Segment Seven sensor may be surrounded or encompass by other sensors that can be used to act as a function switches individual or as a collective sensors to activate other functions when a swipe is carried across two or more sensor.

The sensor maybe used any place where space is limited and a keyboard is needed such as portable telematics devices, control panels on industrial equipment and any other device that requires data entry in any alphanumeric or character based language, particularly if such data entry application does not permit for the eyes to wonder away from the main task. The data entered may be to control a computer menu, a control command or text to fill out data fields in an application. But the main need as envisioned here is to allow critical data entry to be entered while driving, e.g. police officers chasing a suspect and need to input numbers into a computer, or for causal LOL, OMG type of moments Cradle Description Another problem with portable telematics devices such as cellular phones, MP3 players, Satellite Radios, that lead to distraction and accidents is the lack of proper storage The lack of proper universal storage has caused a lot of accidents and deaths and the automakers will not be able to keep up with the diverse portable telematics devices shapes and sizes so for them to offer storage or stowage facility of the portable telematics devices.

The problem with such situation is that the aftermarket devices offered to store those devices are themselves ill fitted to perform the task. For the most, they are flimsy and they depend on being charged by the onboard 12V outlet which adds to the awkwardness of usage and again makes them subject to interfere with the cup holder and contents.

Portable Telematics Hands Free Docking Station For Vehicles and two different HMI Sensors to Control It. Portable Telematics Docking Station For Vehicles which can be universally employed for the operation of different portable devices—that is modular and distinguished with pouch shaped devices holders to securely retain portable devices while charging and to detect that the device is docked in the cradle so operating the device is through Hands Free means.

This inventions deal with stowing and charging one or multiple portable telematics into one smart cradle that can verify that they are housed to assure device charging status and two different sensors to control them to control them. Controlling them includes making and receiving calls and other communications and entertainment devices as well as entering data by gesturing alphanumeric data through the controls.

To keep the devices operating properly drivers usually will have multiple chargers that keep the devices charged. When a call comes in or if the driver wanted to change an audio track, they do not do so Hands Free and they handle the devices so they are distracted by the devices and the wires. When an aftermarket cradle is used to hold a device, usually MP3 player with an FM transmitter or a cell phone, the cradle will hold one device only and the driver is still left with one outlet to dock multiple cradles to charge independently. Many times, the cradles are universal cradles and can barely hold the phone securely in one place during normal driving conditions, so in extreme maneuvers or in case of an accidents the devices are strewn around.

A look through the references shows that the inventors where mainly interested in securing one phone to one place using a universal arm types cradles or in attachments to charge the phone, while as you can tell from the disclosure below, the cradle we are proposing has a pocket type universal docking which makes it more resistant to G forces in case of an impact. On the functionalities side, all cradles accounted for one position to hold the phone and offered no method of controlling the device in a Hands Free Manner while our device center on the Hands Free operations of all the devices docked into the system. Additionally, the cradle offers a module for boosting the signal of transmitting wireless signals and receiving devices and connectivity to the vehicle BUS so the entertainment controls already on many vehicles can be used to select and operate one or more portable telematic device docked into the cradle for operations.

Other references focused on adapting different phones to the same cradle by adding adapters to the phones so they fit the universal part of the cradle (U.S. Pat. No. 5,988,572), or by adapting a single form per each phone solely for the purpose of charging and holding a single portable device in place U.S. Pat. Nos. 6,138,041, 6,889,065, or as is the case with U.S. Pat. Nos. 6,266,542, 6,512,826, 6,751,486, the purpose is to amplify sound and microphone functionalities so the phone allows a person to talk and hear the caller without holding the phone, but nothing is mentioned about securing the phone itself to withstand excessive maneuvers or accident, or to accommodate any additional devices. Other patents dealing with docking a single phone to an adaptive cradle include U.S. Pat. Nos. 6,315,255, 6,341,218, 6,349,223, 6,360,083, 6,366,672, 6,480,378, 6490436491194, 20040102227, 428002, 432530, 467911, D480719, 0494962, D50J 005.

The object of this invention is to provide a universal system to stow drivers' portable devices while they are driving. The system holds the devices via pocket like enclosure that is flexible in shape and can take on the shape of the device inserted firmly. Another system provided here is a system to make sure that the devices are docked thus making sure that the portable devices are being charged.

Another system provided here is a system to control the universal stowing system using one of two methods. The first system is a Segment 7 shaped sensor located at the 10:02 or 9:3. The Segment seven sensor is activated one segment at a time when the driver activate the segment when touched, pressed, temperature activated when traced by a driver digit, for example an index or thumb. The other system is a modular control cluster with each shortcut function as its own module or uses a display that is touch activated and displays a menu where menu items are activated by a touching an icon or a description of a function. Both controlled systems are monitored by a controller that will interpret the driver activation of the sensors to actuate preset controls/interpretations on the cradle to control the docked devices.

Generally, the system describes a Docking system for portable telematics device that is connected to the where the connection to vehicle of claim is to the vehicle electrical system and the vehicle data system, physically through cable or wirelessly and not just mechanically. The system is modular and can add a pouch for larger telematics devices or smaller telematics devices. The system may be configured to require service activation to avail the user from services and upgrades and such activation may require the user to supply financial credit or debit account number and routing number to secure the services and verify the user is the actual owner/purchaser of the cradle and not a person who came to own it illegally or a person that is using a counterfeit cradle Docking the portable telematics to the cradle is mandatory to make sure the portable device is charged so as not to create a distraction during use while driving and to assure a good power to connect to the services. Connecting the device also helps verify which is the driver phone and it will be used to verify that the connected phone via Bluetooth is the phone being docked.

Figure 25:
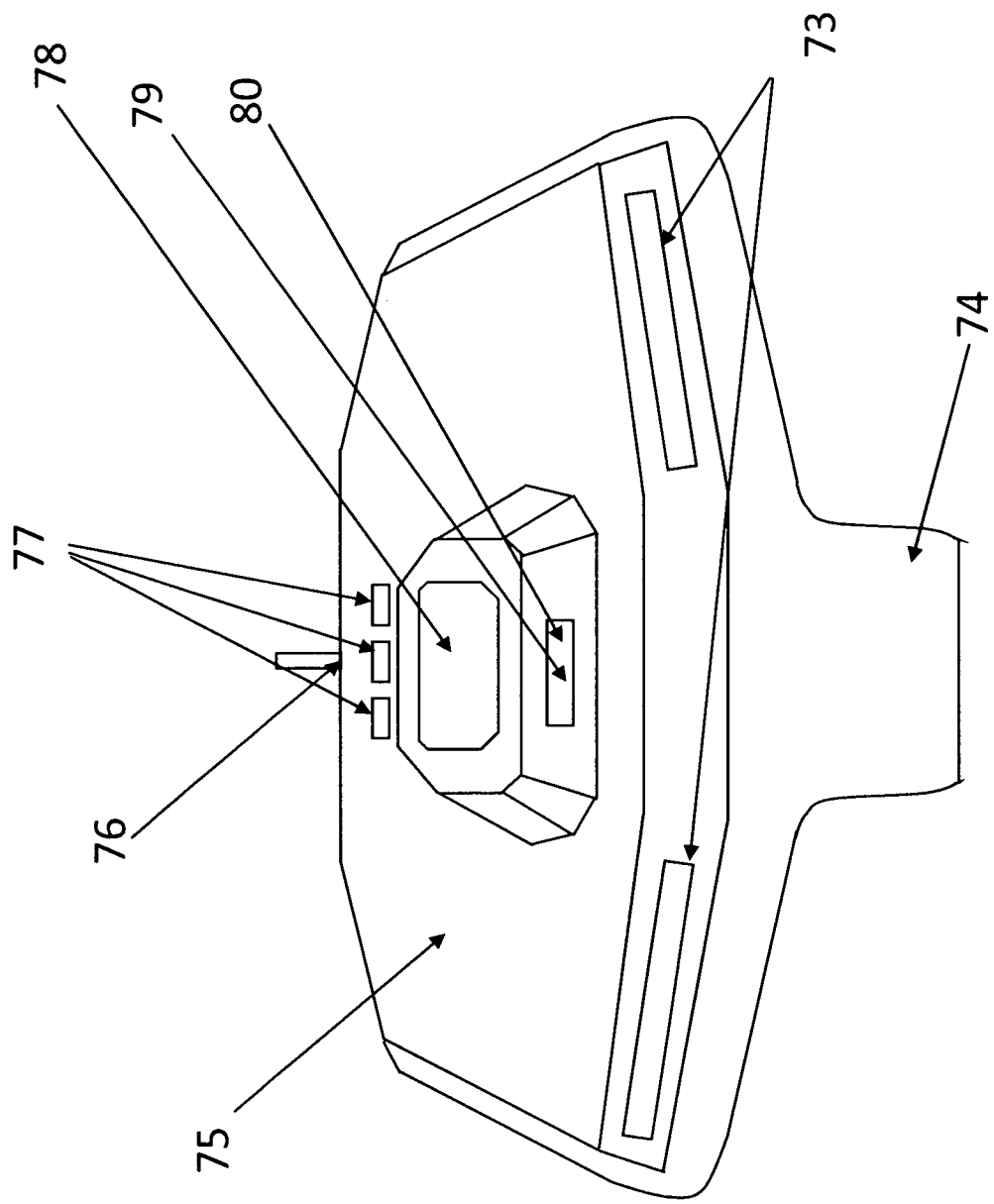
FIG. 25 Shows Cradle Top, Front.
Figure 26:
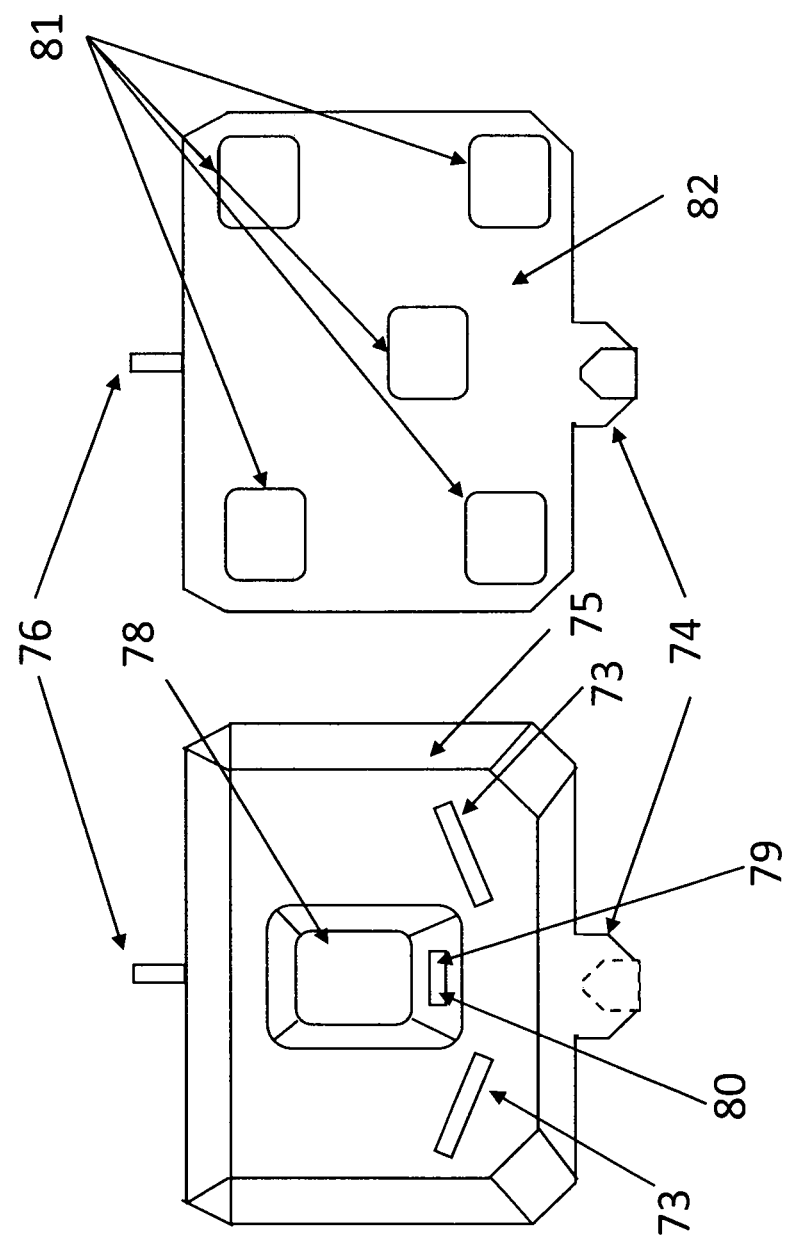
FIG. 26A shows Cradle Top view
FIG. 26B shows Cradle Bottom view

The cradle has an optional display that Smooth transition between one display to the next video display so there is no sudden change in videos display and lead to driver Reflex Distraction and taking the eyes away from the road. The display is also connected to a speaker, a connection to vehicle electric power, wired or wireless connectivity to the vehicle bus and accessories a controller with a memory and programs to control and operate Navigation software, Phone. [internet access via phone or other wireless communication system, CB controls, access to 911, voice recorder, trip recorder, help program, concierge access, vehicle accessories management The following is a list of features that are not fully inclusive and more can be added as this is a modular A pocket shaped cradle. FIG. 25, 73, designed to hold one or more portable telematic device for the purpose of charging and protecting from impact in event of an accident by keeping it firmly in place The pocket shaped cradle is a modular cradle and can add one or more pocket to accommodate multiple devices FIG. 25, 73.

Figure 27:
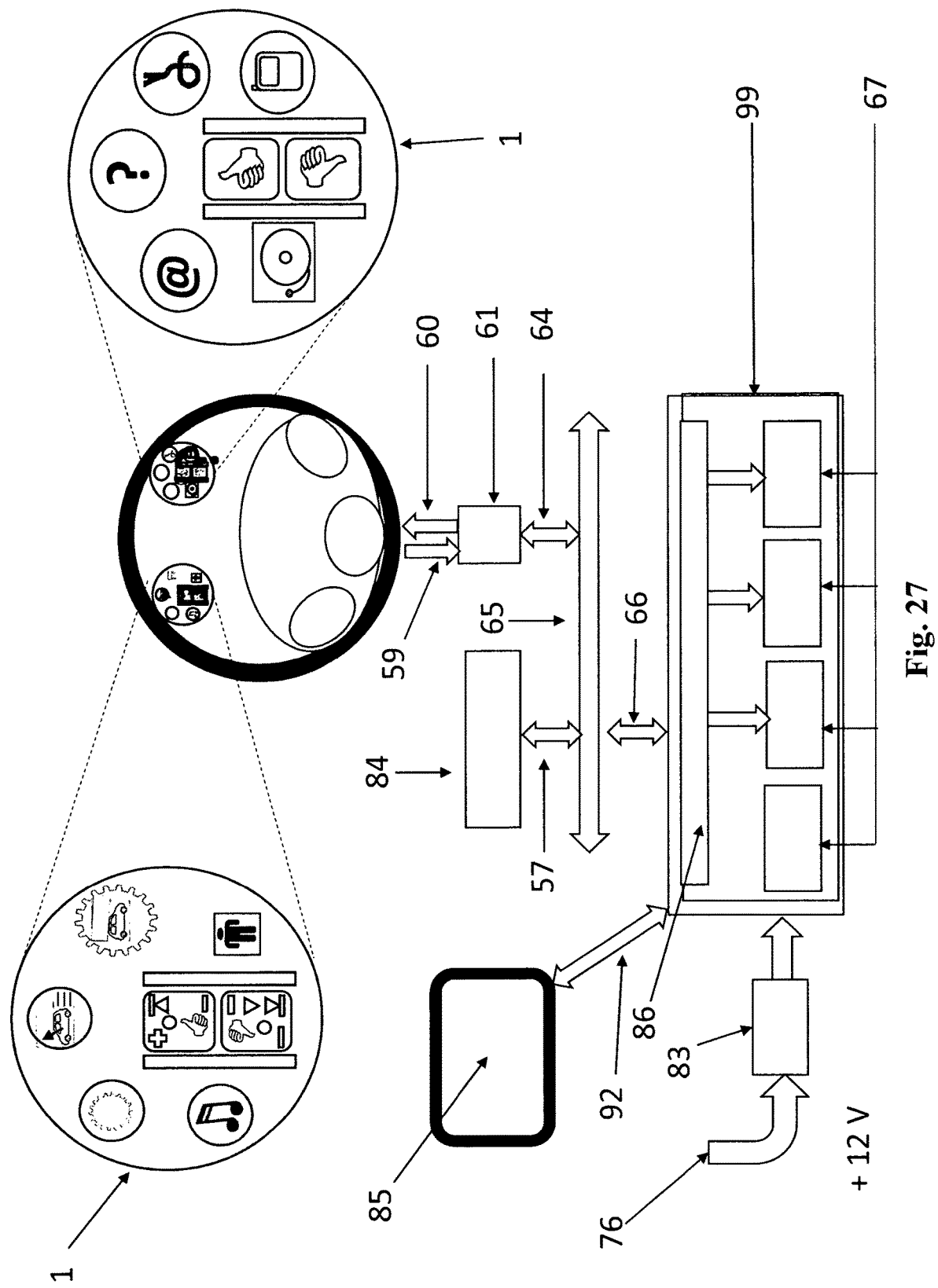
FIG. 27 shows a block diagram of a sensor and cradle and display.

The cradle is connected to the vehicle bus and contains its own CPU, FIG. 27, 86 and the CPU query the Vehicle Bus FIG. 1, 65 Detect number of doors opened and closed and interior noise as well as cellular phone signals to determine who else in the car and if they are teen agers The cradle is equipped with a microphone, FIG. 25, 79 and software that can recognize different voice pitches and will analyze various voices to count passengers and detect animals and children The cradle has an optional display that maybe a portable tablet FIG. 27,85

Figure 28:
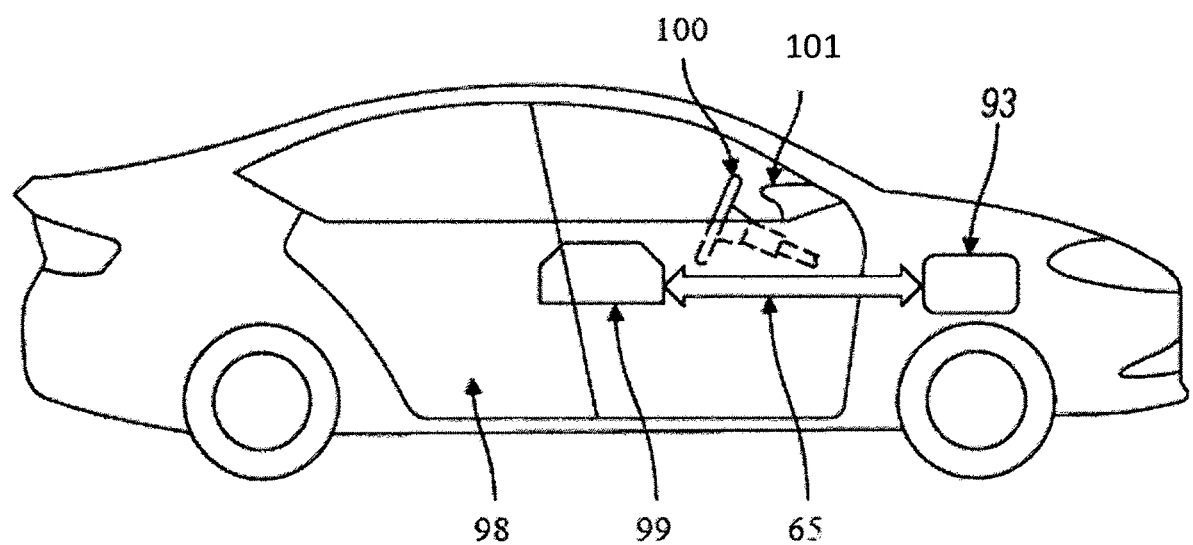
FIG. 28 shows car, steering wheel turn signal and door.

The cradle is also equipped with an optional USB ports. FIG. 25, 77 that can be used to charge devices and the cradle software can be configured so the cradle CPU issues A verbal FIG. 1 63 and visual alarm, FIG. 27,85, to the driver asking to have their devices charged prior to driving and failure to detect the charging may optionally disable the vehicle starter or prevent the shift to drive when a command sent by the cradle FIG. 27, 86 through the vehicle bus FIG. 1, 65, to the vehicle controller FIG. 28 93

The cradle of claim 1 functionalities can be updated with software and hardware to perform additional tasks or functionalities The cradle is monitored by a controller with memory and programs that also accepts plug and play devices using USB, 802.11 Bluetooth or ZigBee The controller can make sure that a specific device that is wirelessly plugged into the cradle is physically plugged into the cradle by detecting power draw from the specific device and verifying the status via the wireless connection. The controller will cutoff power then monitors the effect through the wireless connection to verify the change in status Another method of verifying connectivity is by calling the phone and verifies that it is receiving the call at the same phone by going directly to voice mail or by detecting a caller ID from its own calling source The cradle can further determine if the device physically charging is the device wirelessly docked to the cradle by turning off the power to the connected device and then watching the status wirelessly to see if the wirelessly y connected device looses power as well If the telematic device from 1 is not connected the cradle will issue an audible, visual and data signal detectable inside and/or outside the vehicle The cradle is supplied with at least one speaker FIG. 25, 78 that will provide audible feedback for text messages, e-mails or web pages being read to the driver using text to speech residing on the cradle or at a portal The cradle contain modules to accommodate satellite radios, HD radios, CB, FIG. 27.67 radios or other communication or infotainment device that plug into the cradle physically or wirelessly and such devices output is broadcasted through the car speakers physically or wirelessly.

Cradle if not built-in to the vehicle, it may optionally be attachable and removable to the vehicle, permanently y attachable or built into the vehicle using adhesive or Velcro, FIGS. 26, 81 and 74 and 82

The cradle can be controlled remotely using any of the steering wheel buttons.

FIG. 1, 1 or other built in vehicle controls.

The cradle can be a mounted on vertical surface or on horizontal surface or integrated permanently into the interior of the vehicle The cradle will emit a signal detectable inside and/or outside the vehicle when the ignition is started to remind the driver to dock the equipment physically. FIG. 25, 78

The cradle will emit a signal detectable inside and outside the vehicle to remind the driver to pick up the docked devices when the driver door is opened or when the ignition is turned off FIG. 25, 78

The cradle will have a mechanism to grab the portable devices physically magnetically, vacuum, pneumatic bladder to squeeze the device in the pocket, elastic ribbon or pocket to grab the device tightly, bimetal effected by electricity that tighten a ribbon or the pocket around the portable devices The cradle will prevent t the car from starting or will start the car with limited capabilities, e.g. top speed, second gear only if a telematic device is not plugged in and may issue a signal detectable inside or outside the vehicle declaring the vehicle is in use without a telematics device plugged in.

At least one part of the pocket maybe made of elastic material

The cradle controller will monitor for changes in the voltage for power supply to determine changes in the vehicle status, e.g. increased rpm, shifting in transmission via vehicle bus, FIG. 1, 65

The cradle will use G sensor to determine acceleration deceleration, shift shock and counting the gears as well as determining directions, Not Shown The cradle will accept a profile of a driver with policy and preferences from the phone, the web or as an email and will compress the profile that is not presently y in the car to make room for the profile of the person currently in the car. Not shown The cradle CPU FIG. 27, 86 will suppress unnecessary announcement from navigation e.g. if the driver gives turn signal FIG. 28, 101 the navigation does not repeat announcement annoying the driver telling him to take a turn Cradle will be woken up automatically upon hearing a specific frequency through its microphone, FIG. 25, 79 or upon shaking the vehicle (G sensor not shown)

When the cradle wakes up from it will wait for a wireless transmission with a code to open the doors When the cradle wakes up from it will wait for a serious on clicks on the glass to open the door.

Driver can Override

Cradle may optionally have a screen to display prompts and messages

The cradle may optionally be equipped with signal booster for cellular phone signal or with antennas for other receiver type devices including GPS antenna.

When system taps directly to the sensor will monitor for changes in the voltage to determine changes in the vehicle status The device has a semi privacy mode where a driver can remotely select to use an ear piece to listen to messages, music or a stealth conversation without disturbing others in the cars such as a sleeping baby.

Cradle interface with devices and allows for control of applications on devices

Cradle has a speech recognition and text to speech application that allows a driver to get audible feedback, listen to text being read and issue verbal commands to the cradle and record voice notes and conversations.

Pocket

May be fully built in

May be a module, that is removable/exchangeable for various devices

May be just a rubber band that runs across the body of the portable device.

Read SIM and emulate phone

Convert desktop info (calendar, phone book) to cradle specific information and update the profile contents on the phone Location on top of IP (Preferably)

Remotely controlled

Controlled by speech recognition

Plug and play

Drivers for devices from the internet

Bottom glue tape is at a surface that is concave to the bottom side surface and a slight pressure from the top surface will push the double tape toward the vehicle surface to create the bond. This will help p the installer to position the cradle to their liking and then simply glue it in place without messing around with it.

Modular so it can add other component, e.g. wireless modems, second phone. CB module, Satellite Radio, MP3 player pocket, etc. etc.

After bump/accident is sensed from a G sensor; Did the engine stay on? Did the vehicle move? For how long? Did the gear change? These will indicate that the bump was not a collision and just a passing phenomenon, e.g. pothole The cradle is equipped with a batter that operated a microphone and a sound detection circuit, a light detection circuit or a wireless detection circuit when the vehicle is off When the circuit t detects a pre-specified sound, light or wireless signature, the circuit will wake cradle up, and the door will be unlocked.

Speaker Cradle will not be high pitch so as not to be distracting and can be adjusted by the user for volume and pitch, bass and treble Count passengers by steering wheel buckles, door opening, seat sensors and Bluetooth devices detections or cellular signal detection The cradle can access the vehicle sound system through the vehicle bus, direct wired connection or wirelessly The cradle navigation can receive new route instruction from a remote controller via text, email, and ftp or by logging into a web page to retrieve updated directions.

The phone connects to the cradle using the IP

The cradle Verbally announce incoming communication

The cradle Verbally announce menu selection

When the cradle is an add-on and not an integrated part of the vehicle, the Bottom of cradle contains depressions with double tape. Velcro or similar temporary attachment material. Pressing the upper surface of the cradle after positioning the cradle will forces the tape out of the depression and will cause the tape to stick to the surface Cradle my use the phone as a modem or may have a dedicated cellular or LAN or WAN or Satellite communication integrated or added on as a module to communicate with remote controllers or for voice communications.

The cradle is controlled by touch sensitive displays located @ the 10:02—The displays show icons based menu to be selected from and selecting an icon will show the next menu where the icons are short cuts to the menus of equipment and accessories controlled by the cradle.

Cradles can add new module for different driving and communication services and utilities functionality like full time internet access, reverse camera, forward collision warming camera, blind spot camera, lane departure warning camera, breathalyzer The cradle has at least one light to show status of various functionalities and an optional display FIG. 27, 85 for Navigations and caller ID or menu display that may substitute for the status lights Other embodiments are possible as the design preferences limited by cost or the driving application or the business or safety case for the devices varies.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. Similarly, specific features or components described in the different embodiments of the steering wheel vehicle safety control system may be used with other embodiments or may be combined with yet other features or components to form other embodiments. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The preferred embodiment of the present invention has been disclosed. A person of ordinary skill in the art would realize however, that certain modifications would come within the teachings of this invention. Therefore, the following claims should be studied to determine the true scope and content of the invention.

What is claimed:

1. A driver operated Hands On Wheel control system for managing applications on a telematic controller with built in memory, input and output means and communication protocols comprising:
    (a) at least one touch sensitive display module, the display in communication with the telematic controller and disposed on a steering wheel and accessible by the driver of a vehicle while the driver's hand remains on the steering wheel while touching the display with a driver digit;
    (b) one or more distinct icons displayed on the touch sensitive display for activating at least one application on said telematic controller, wherein the icons section is a stored driver preference; and
    (c) one or more icon functions for affirming or rejecting telematic controller communication.

2. The control system of claim 1 wherein the controller is a built-in vehicle device or a portable telematic communication device.

3. The control system of claim 2, wherein the driver preferences are stored in the telematic controller memory.

4. The control system of claim 1, including driver preferences inputted into the controller memory, and
    wherein the driver preferences includes one or more condition factors as in current function factors, commands or menu selection factors, applications loaded on the controller factor, temporal factors, environmental factors, traffic factors, preset parental or employer presets, or driver license type factor, or any combination thereof.

5. The control system of claim 1, wherein the memory includes submenus, options, or commands each of which are static in structure or arranged in a dynamic order dependent upon condition factors.

6. The control system of claim 1, wherein the disposition of the touch sensitive display module is interchangeable with at least one other touch display module.

7. The control system of claim 1 wherein the touch sensitive display module is in communication with the telematic controller through either a physical data bus protocol or a wireless protocol and may include icons to control vehicle equipment via the vehicle.

8. The control system of claim 1, wherein the touch display module is removable.

9. The control system of claim 1, wherein the touch sensitive display comprises two regions, the first region having one or more shortcut icons and the second region is reserved for gesture response.

10. The control system of claim 9, wherein the system is a multimodal input system wherein speech and touch are used to provide input to the controller, and further wherein the selecting or the activating of the one or more shortcut actuators enhances the reliability of speech or gesture recognition by the control system, and further wherein the possible span of received speech or gesture recognition responses from the driver is reduced to speech or gesture patterns associated with the selected or activated icon.

11. The control system of claim 1, wherein the touch sensitive display provides at least one of distinct haptic feedback, verbal feedback, visual feedback, or any combination thereof.

12. The control system of claim 1, wherein the touch sensitive display provides distinct haptic feedback in one or more pulses of different amplitudes over different time spans based upon the driver response or selection.

13. The control system of claim 1, wherein the haptic feedback varies as an inverse of the sequence of the pulse.

14. The control system of claim 1, wherein the touch sensitive display includes one or more virtual barriers which separates the icons area from a gesture response area, further wherein the virtual barriers provide distinct haptic feedback when a digit of the driver crosses said virtual barrier, and further wherein said distinct haptic feedback is distinguishable based upon one or more pulses of different amplitudes over different time spans, further wherein said haptic feedback varies as an inverse of the sequence of the pulse when the gesture crosses said barrier in a reverse direction.

15. The control system of claim 1, wherein the disposition or orientation of the touch sensitive display is adjustable in relation to the steering member.

16. The control system of claim 1, wherein the system is responsive to a swipe across at last two consecutive icons and wherein the response will vary by at least the number of icons swiped, the direction of the swipe and the initial icon activated.

17. The control system of claim 1, wherein the telematic controller has voice input and speech recognition software to process driver verbal input.

18. The control system of claim 1 which further comprises a data bus, the telematic controller being in communication with the data bus.

19. A method for controlling a communication system on a vehicle having a plurality of equipment and applications controlling communication running on a telematic controller comprising:
 a touch sensitive display in communication with a telematic controller, displaying icons for preferred driver application that can be simultaneously touched by a driver digit by the same hand controlling the steering wheel with icons dedicated to affirming or rejecting a telematic controller communication.

* * * * *